United States Patent
Jeanguenat et al.

(10) Patent No.: US 6,391,918 B1
(45) Date of Patent: May 21, 2002

(54) N-SULPHONYL AND N-SULPHINYL PHENYLGLYCINAMIDE

(75) Inventors: André Jeanguenat, Basel; Martin Zeller, Baden, both of (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/623,160

(22) PCT Filed: Feb. 25, 1999

(86) PCT No.: PCT/EP99/01216

§ 371 Date: Aug. 25, 2000

§ 102(e) Date: Aug. 25, 2000

(87) PCT Pub. No.: WO99/43644

PCT Pub. Date: Sep. 2, 1999

(30) Foreign Application Priority Data

Feb. 27, 1998 (GB) ............................................. 9804265

(51) Int. Cl.$^7$ ........................ A61K 31/16; A61K 31/18; A61K 31/35; A61K 31/34

(52) U.S. Cl. ..................... 514/600; 514/347; 514/367; 514/415; 514/424; 514/445; 514/459; 514/471; 514/552; 514/604; 514/605; 514/607; 514/539; 514/542; 560/13; 546/265; 549/65; 549/419; 549/494; 558/413

(58) Field of Search .................. 514/347, 367, 514/415, 424, 445, 459, 471, 552, 539, 542, 600, 607, 604, 605; 546/265; 548/166, 477, 542; 549/65, 419, 494; 558/413; 560/13; 564/79, 84, 85, 86, 87, 88, 89, 90, 91, 97, 99

(56) References Cited

U.S. PATENT DOCUMENTS 6,221,888 B1 * 4/2001 Durette et al. .............. 514/357

FOREIGN PATENT DOCUMENTS

| EP | 0 493 683 | 7/1992 |
|----|-----------|--------|
| WO | WO 95/30651 | 11/1995 |
| WO | WO 98/38160 | 9/1998 |

* cited by examiner

*Primary Examiner*—Peter O'Sullivan
(74) *Attorney, Agent, or Firm*—William A. Teoli, Jr.

(57) ABSTRACT

Novel α-amino acid amides of formula (I) as well as possible isomers and mixtures of isomers thereof, wherein the substituents are defined as follows: n is the number zero or one; $R_1$ is optionally substituted alkyl, alkenyl, alkynyl, cycloalkyl, cycloalkylalkyl, aryl or arylalkyl; or a group $NR_aR_b$, wherein $R_a$ and $R_b$ are each independently of the other hydrogen, alkyl or form together an alkylene bridge; $R_2$ is hydrogen or alkyl; $R_3$ is optionally substituted aryl or heteroaryl; A is alkylene; and B is optionally substituted aryl; with the exception of the following compounds 2-phenyl-N-(1-phenyl-ethyl)-2-(4-methylphenyl)-sulfonylamino-acetamide, 2-phenyl-N-(1-phenyl-ethyl)-2-(4-chlorophenyl)-sulfonylamino-acetamide, 2-phenyl-N-(1-phenyl-ethyl)-2-(4-nitrolphenyl)-sulfonylamino-acetamide, 2-phenyl-N-(1-phenyl-ethyl)-2-(4-methoxyphenyl)-sulfonylamino-acetamide, 2-phenyl-N-(1-phenyl-ethyl)-2-(4-fluorophenyl)-sulfonylamino-acetamide, 2-phenyl-N-(1-phenyl-ethyl)-2-phenyl-sulfonylamino-acetamide and 2-phenyl-N-(1-phenyl-ethyl)-2-methane-sulfonylamino-acetamide. The novel compounds have plant-protective properties and are suitable for protecting plants against infestations by phytopathogenic microorganisms, in particular fungi.

(I)

$$R_1 - \underset{(O)_n}{\underset{\|}{S}} - NH - \underset{R_3}{\overset{R_2}{C}} - \underset{\|}{\overset{O}{C}} - NH - A - B$$

11 Claims, No Drawings

N-SULPHONYL AND N-SULPHINYL PHENYLGLYCINAMIDE

This application is a 371 of international application PCT/EP99/01216, filed Feb. 25, 1999.

The present invention relates to novel α-amino acid amides of formula I below. It relates to the preparation of those substances and to agrochemical compositions that comprise at least one of those compounds as active ingredient. The invention also relates to the preparation of the said compositions and to the use of the active ingredients or the compositions in the control or prevention of plant infestation by phytopathogenic microorganisms especially fungi.

The compounds according to the invention correspond to the general formula I

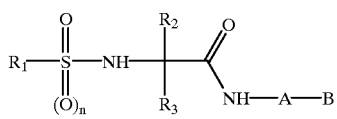

as well as possible isomers and mixtures of isomers thereof,
wherein the substituents are defined as follows:
n is the number zero or one;
$R_1$ is optionally substituted alkyl, alkenyl, alkynyl, cycloalkyl, cycloalkylalkyl, aryl or arylalkyl; or a group $NR_aR_b$ wherein $R_a$ and $R_b$ are each independently of the other hydrogen, alkyl or form together an alkylene bridge;
$R_2$ is hydrogen or alkyl;
$R_3$ is optionally substituted aryl or heteroaryl;
A is alkylene; and
B is optionally substituted aryl;
with the exception of the following compounds
2-phenyl-N-(1-phenyl-ethyl)-2-(4-methylphenyl)-sulfonylamino-acetamide,
2-phenyl-N-(1-phenyl-ethyl)-2-(4-chlorophenyl)-sulfonylamino-acetamide,
2-phenyl-N-(1-phenyl-ethyl)-2-(4-nitrophenyl)-sulfonylamino-acetamide,
2-phenyl-N-(1-phenyl-ethyl)-2-(4-methoxyphenyl)-sulfonylamino-acetamide,
2-phenyl-N-(1-phenyl-ethyl)-2-(4-fluorophenyl)-sulfonylamino-acetamide,
2-phenyl-N-(1-phenyl-ethyl)-2-phenyl-sulfonylamino-acetamide and
2-phenyl-N-(1-phenyl-ethyl)-2-methane-sulfonylamino-acetamide.

The above alkyl, alkenyl, alkynyl, cycloalkyl, cycloalkylalkyl, aryl, arylalkyl or heteroaryl groups may carry one or more identical or different substituents. Normally not more than five substituents in each of these groups are present at the same time. Examples of substituents of these groups are: alkyl, alkenyl, alkynyl, cycloalkyl, cycloalkylalkyl, phenyl and phenylalkyl, it being possible in turn for all of the preceding groups to carry one or more identical or different halogen atoms; alkoxy; alkenyloxy; alkynyloxy; alkoxyalkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl; alkynyloxycarbonyl.

In the above formula I, "halogen" includes fluorine, chlorine, bromine and iodine, preferably fluorine, chlorine or bromine.

The alkyl, alkenyl and alkynyl radicals may be straight-chain or branched, this applying also to the alkyl, alkenyl or alkynyl moiety of other groups containing alkyl, alkenyl or alkynyl.

Depending on the number of carbon atoms mentioned, alkyl on its own or as part of another substituent is to be understood as meaning, for example, methyl, ethyl, propyl, butyl, pentyl, n-hexyl, n-heptyl, n-octyl, n-decyl, n-dodecyl and the isomers thereof, such as isopropyl, isobutyl, tert-butyl, sec-butyl, tert-amyl, 1-ethyl-hexyl, n-octyl, n-nonyl or n-decyl. Cycloalkyl denotes, depending on the number of carbon atoms mentioned, cyclopropyl, cyclobutyl, cyclopentyl, cyclohexyl, cycloheptyl or cyclooctyl.

Alkenyl will be understood as meaning straight-chain or branched alkenyl such as allyl, vinyl, methallyl, 1-methylvinyl, but-2-en-1-yl, pent-2-en-1-yl or hex-2-en-1-yl. Preferred alkenyl radicals contain 3 to 4 carbon atoms in the chain.

Alkynyl can likewise, in accordance with the number of carbon atoms, be straight-chain or branched and is typically propargyl, but-2-yl-1-yl, but-1-yn-3-yl, pent-2-yn-1-yl or hex-2-yn-1-yl. The preferred meaning is propargyl.

A haloalkyl group may have one or more (identical or different) halogen atoms, such as, for example, $CHCl_2$, $CH_2F$, $CCl_3$, $CClF_2$, $CH_2Cl$, $CHF_2$, $CF_3$, $CH_2CH_2Br$, $CH_2CF_3$, $CH_2CH_2F$, $C_2Cl_5$, $CH_2Br$, $CHBrCl$, $CH_2CH_2CF_3$ etc.

Alkoxy is typically methoxy, ethoxy, propyloxy, isopropyloxy, n-butyloxy, isobutyloxy, sec-butyloxy and tert-butyloxy. Methoxy and ethoxy are preferred.

Alkylthio is typically methylthio or ethylthio.

Haloalkoxy is any alkoxy substituted with one or more halogen atoms. Typical examples are difluoromethoxy, trifluoromethoxy, 2,2,-trifluoroethoxy, 1,1,2,2-tetrafluoroethoxy, 2-fluoroethoxy, 2-chloroethoxy and 2,2-difluoroethoxy.

Aryl can be for example phenyl or naphthyl.

Arylalkyl can be for example benzyl, 2-phenyl-ethyl or 3-phenyl-propyl.

Heteroaryl stands for aromatic ring systems comprising mono-, bi- or tricyclic systems wherein at least one oxygen, nitrogen or sulfur atom is present as a ring member. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotroazolyl, benzothiazolyl, benzoxazolyl, quinolinyl, isoquinolinyl, phthalazinyl, quinoxalinyl, quinazolinyl, cinnolinyl and naphthyridinyl.

Alkanoyl is, in accordance with the number of carbon atoms embraced, either straight-chain or branched. Typical examples are formyl, acetyl, propionyl, butyryl or pivaloyl.

As a result of the presence of at least one asymmetric carbon atom and/or at least one asymmetric sulfur atom in the compounds of formula I the compounds may occur in the form of optical isomers. Owing to the presence of an aliphatic —C=C— double bond, geometrical isomerism may also occur. Formula I is intended to encompass all of those possible isomeric forms and mixtures thereof.

Preference is given to compounds of formula I wherein
n is the number zero or one;
$R_1$ is $C_1$–$C_{10}$alkenyl, $C_2$–$C_{10}$alkenyl, $C_2$–$C_{10}$alkynyl, $C_3$–$C_8$cycloalkyl, $C_3$–$C_8$cycloalkyl-$C_1$–$C_6$alkyl, $C_6$–$C_{10}$aryl, or $C_6$–$C_{10}$aryl-$C_1$–$C_6$alkyl that are optionally mono- or poly-substituted by $C_1$–$C_8$alkyl, $C_1$–$C_8$alkoxy, $C_1$–$C_8$alkylthio, $C_1$–$C_8$alkylsulfonyl, $C_3-C_8$cycloalkyl, $C_1-C_8$alkoxycarbonyl, $C_3-C_8$alkenyloxycarbonyl, $C_3-C_8$alkynyloxycarbonyl, $C_3-C_8$cycloalkyl-$C_1-C_6$alkyl, $C_2-C_8$alkenyl, $C_2-C_8$alkynyl, $C_3-C_8$alkenyloxy, $C_3-C_8$alkynyloxy, $C_1-C_8$alkanoyl (where all these alkyl, alkenyl, alkynyl or cycloalkyl containing groups may be partially or fully halogenated), halogen, cyano or nitro; or a group $NR_aR_b$, wherein $R_a$ and $R_b$ are each independently of the other hydrogen, $C_1-C_8$alkyl or together are $C_2-C_7$alkylen;

$R_2$ is hydrogen or $C_1-C_8$alkyl;

$R_3$ is phenyl, naphthyl or heteroaryl formed by 1 or 2 five- or six-membered rings containing 1 to 4 identical or different heteroatoms selected from oxygen, nitrogen or sulfur and are optionally mono- or poly-substituted by $C_1-C_8$alkyl, $C_2-C_8$alkenyl, $C_2-C_8$alkynyl, $C_1-C_8$alkoxy, $C_1-C_8$alkylthio, $C_1-C_8$alkylsulfonyl, $C_3-C_8$cycloalkyl, $C_3-C_8$cycloalkyl-$C_1-C_6$alkyl, $C_1-C_4$alkylendioxy, $C_1-C_8$alkoxycarbonyl, $C_3-C_8$alkenyloxycarbonyl, $C_3-C_8$alkynyloxycarbonyl, $C_3-C_8$cycloalkyloxy, $C_3-C_8$alkenyloxy, $C_3-C_8$alkynyloxy, $C_1-C_8$alkanoyl, $C_1-C_8$dialkylamino, $C_1-C_8$alkylamino (where all these alkyl alkenyl, alkynyl or cycloalkyl containing groups may be partially or fully halogenated), halogen, nitro, cyano, hydroxy or amino;

A is $C_1-C_8$alkylen; and

B is phenyl optionally mono- or poly-substituted by $C_1-C_8$alkyl, $C_2-C_8$alkenyl, $C_2-C_8$alkynyl, $C_1-C_8$alkoxy, $C_1-C_8$alkylthio, $C_1-C_8$alkylsulfonyl, $C_3-C_8$cycloalkyl, $C_3-C_8$cycloalkyl-$C_1-C_6$alkyl, $C_1-C_8$alkoxycarbonyl, $C_3-C_8$alkenyloxycarbonyl, $C_3-C_8$alkynyloxycarbonyl, $C_3-C_8$cycloalkyloxy, $C_3-C_8$alkenyloxy, $C_3-C_8$alkynyloxy, $C_1-C_8$alkanoyl, $C_1-C_8$dialkylamino, $C_1-C_8$alkylamino, $C_6-C_{10}$aryloxy, $C_6-C_{10}$aryl-$C_1-C_6$alkoxy, $C_6-C_{10}$aryl-$C_1-C_6$alkenyloxy, $C_6-C_{10}$aryl-$C_1-C_6$alkynyloxy, $C_1-C_8$alkanoyloxy (where all these alkyl alkenyl, alkynyl or cycloalkyl containing groups may be partially or fully halogenated and where all aryl containing groups may be optionally mono- or poly-substituted by $C_1-C_8$alkyl, $C_2-C_8$alkenyl $C_3-C_8$cycloalkyl, $C_1-C_8$alkoxy, $C_1-C_8$alkylthio, $C_1-C_8$alkoxycarbonyl $C_1-C_8$halogenalkyl, $C_1-C_8$halogenalkoxy, $C_1-C_8$halogenthioalkyl, halogen nitro or cyano), halogen, nitro, cyano, hydroxy, amino or the phenyl group may be substituted in two adjacent positions by $C_1-C_4$alkylenedioxy wherein the alkylene part may be substituted by halogen (sub-group A).

Within the scope of sub-group A, special mention should be made of those compounds of formula I wherein n is the number zero or one;

$R_1$ is $C_1-C_{10}$alkyl $C_2-C_{10}$alkenyl, $C_3-C_8$cycloalkyl that are optionally mono- or poly-substituted by $C_1-C_8$alkyl, $C_1-C_8$alkoxy, $C_1-C_8$alkylthio, $C_1-C_8$alkanoyl, $C_1-C_8$alkoxycarbonyl, $C_1-C_8$halogenalkyl, $C_1-C_8$halogenalkoxy, $C_1-C_8$halogenalkylthio, halogen, nitro or cyano; or a group $NR_aR_b$, wherein $R_a$ and $R_b$ are each independently of the other hydrogen, $C_1-C_8$alkyl, or together are tetramethylene or pentamethylene;

$R_2$ is hydrogen or methyl;

$R_3$ is phenyl, naphthyl, furyl, thienyl, imidazolyl, thiazolyl, oxazolyl, pyridyl, pyrimidinyl, benzothiophenyl, benzothiazolyl, chinolinyl, pyrazolyl, indolyl, benzimidazolyl or pyrrolyl optionally substituted by 1 to 3 substituents selected from $C_1-C_8$alkyl, $C_2-C_8$alkenyl, $C_3-C_8$cycloalkyl, $C_1-C_8$alkoxy, $C_1-C_8$alkylthio, $C_1-C_8$alkoxycarbonyl, $C_1-C_8$halogenalkyl, $C_1-C_8$halogenalkoxy, $C_1-C_8$halogenalkylthio, halogen, hydroxy, nitro or cyano;

A is $C_1-C_4$alkylen; and

B is phenyl optionally substituted by 1 to 3 substituents selected from $C_1-C_8$alkyl, $C_1-C_8$alkoxy, $C_3-C_8$alkenyloxy, $C_3-C_8$alkynyloxy, phenyl-$C_1-C_6$alkyloxy, phenyl-$C_3-C_6$alkenyloxy, phenyl-$C_3-C_6$alkynyloxy, $C_1-C_8$alkylthio, $C_1-C_8$alkoxycarbonyl, $C_1-C_8$halogenalkoxy, $C_3-C_8$halogenalkenyloxy, halogen, hydroxy, nitro or cyano (where all phenyl containing groups may be optionally substituted by 1 to 3 substituents selected from $C_1-C_8$alkyl, $C_1-C_8$alkoxy, $C_1-C_8$alkylthio, $C_1-C_8$halogenalkyl, $C_1-C_8$halogenalkoxy, $C_1-C_8$halogenthioalkyl, halogen or cyano) (sub-group B).

An important group is formed by compounds of formula I wherein n is the number one;

$R_1$ is $C_1-C_6$alkyl, $C_2-C_{10}$alkenyl, $C_5-C_6$cycloalkyl, that are optionally mono- or poly-substituted by $C_1-C_8$alkyl, $C_1-C_8$alkoxy, $C_1-C_8$alkoxycarbonyl, $C_1-C_8$halogenalkyl, $C_1-C_8$halogenalkoxy, halogen or cyano; or a group $NR_aR_b$, wherein $R_a$ and $R_b$ are each independently of the other methyl or ethyl;

$R_2$ is hydrogen;

$R_3$ is phenyl optionally substituted by 1 to 3 substituents selected from $C_1-C_8$alkyl, $C_2-C_8$alkenyl, $C_3-C_8$cycloalkyl, $C_1-C_8$alkoxy, $C_1-C_8$alkylthio, $C_1-C_8$alkoxycarbonyl, $C_1-C_8$halogenalkyl, $C_1-C_8$halogenalkoxy, $C_1-C_8$halogenthioalkyl, halogen, hydroxy, nitro or cyano;

A is ethylen; and

B is phenyl optionally substituted by 2 to 3 substituents selected from $C_1-C_8$alkyl, $C_1-C_8$alkoxy, $C_3-C_8$alkenyloxy, $C_3-C_8$alkynyloxy, phenyl-$C_1-C_6$alkyloxy, phenyl-$C_3-C_6$alkenyloxy, phenyl-$C_3-C_6$alkynyloxy, $C_1-C_8$alkylthio, $C_1-C_8$alkoxycarbonyl, $C_1-C_8$halogenalkoxy, $C_3-C_8$halogenalkenyloxy, halogen, hydroxy, nitro or cyano (where all phenyl containing groups may be optionally substituted by 1 to 3 substituents selected from $C_1-C_8$alkyl, $C_1-C_8$alkoxy, $C_1-C_8$alkylthio, $C_1-C_8$halogenalkyl, $C_1-C_8$halogenalkoxy, $C_1-C_8$halogenthioalkyl, halogen or cyano) (sub-group C).

A special group within the scope of sub-group C comprises compounds of formula I wherein n is the number one;

$R_1$ is $C_1-C_4$alkyl optionally mono- or poly-substituted by fluorine, chlorine, bromine or dimethylamin;

$R_2$ is hydrogen;

$R_3$ is phenyl optionally substituted by 1 to 3 substituents selected from $C_1-C_8$alkyl, $C_2-C_8$alkenyl, $C_3-C_8$cycloalkyl, $C_1-C_8$alkoxy, $C_1-C_8$alkylthio, $C_1-C_8$alkoxycarbonyl, $C_1-C_8$halogenalkyl, $C_1-C_8$halogenalkoxy, $C_1-C_8$halogenthioalkyl, halogen, nitro or cyano;

A is ethylen; and

B is a group

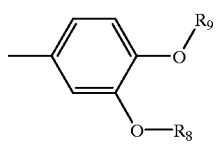

wherein $R_8$ is $C_1$–$C_4$alkyl, and $R_9$ is $C_1$–$C_8$alkyl, $C_3$–$C_8$alkenyl, $C_3$–$C_8$alkynyl, phenyl-$C_1$–$C_6$alkyl, phenyl-$C_3$–$C_6$alkenyl, phenyl-$C_3$–$C_6$alkynyl, $C_1$–$C_8$halogenalkyl, $C_3$–$C_8$halogenalkenyl (where all phenyl containing groups may be optionally substituted by 1 to 3 substituents selected from $C_1$–$C_8$alkyl, $C_1$–$C_8$alkoxy, $C_1$–$C_8$alkylthio, $C_1$–$C_8$halogenalkyl, $C_1$–$C_8$halogenalkoxy, $C_1$–$C_8$halogenthioalkyl, halogen or cyano) (sub-group Ca).

Certain α-amino acid derivatives having a different kind of structure have already been proposed for the control of plant-destructive fungi (for example in EP-398 072, EP-425925, DE-40 26 966, EP-477 639, EP-493 683, DE-40 35 851, EP-487 154, EP-496239, EP-550 788 and EP-554729). Those compositions are not, however, satisfactory in their action. Surprisingly, with the compound structure of formula I, new kinds of microbicides having a high activity have been found.

DESCRIPTION OF THE PROCESS FOR THE PREPARATION OF COMPOUNDS ACCORDING TO THE INVENTION

The compounds of formula I can be prepared by one of the following processes:

dicyclohexylcarbodiimide, carbonyldiimidazole, O-(benzotriaz-1-yl)-N,N,N',N'-bis(pentamethylene) uronium hexafluorophosphate, O-(benzotriaz-1-yl)-N,N,N',N'-bis(tetramethylene)uronium hexafluorophosphate, (benzotriazol-1-yloxy)-tripyrrolidinophosphonium hexafluorophosphate, (benzotriazol-1-yloxy)-tris(dimethylamino)phosphonium hexafluorophosphate or O-(benzotriazol-1-yl)-N,N,N',N'-tetramethyluronium hexafluorophosphate).

The acid halides corresponding to the amino acid of formula II can be prepared by reacting the amino acid of formula II in a manner known per se with a halogenating agent, for example phosphorus pentachloride, thionyl chloride, oxalyl chloride, cyanuric fluoride or diethylaminosulfur trifluoride.

The mixed anhydrides corresponding to the amino acid of formula II can be prepared by reacting the amino acid of formula II with chloroformic acid esters, for example chloroformic acid alkyl esters preferably chloroformic acid isobutyl ester, in the absence or presence of an acid-binding agent, such as an inorganic or organic base, for example a tertiary amine, e.g. triethylamine, pyridine, N-methylpiperidine or N-methylmorpholine.

Step A: The compounds of formula II can be prepared by reaction of an amino acid of formula IV where $R_2$ and $R_3$ have the same meanings as defined above with a sulfonyl halide or a sulfinyl halide of formula III where $R_1$ and n have the meanings as defined above and where X is halide, preferentially chlorine or bromine. The reaction is optionally performed in a solvent and in presence of a base.

a)

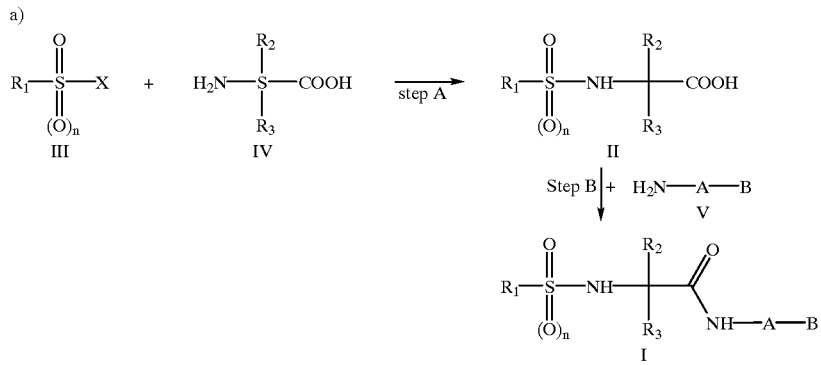

Step B: An amino acid of formula II or a carboxy-activated derivative of an amino acid of formula II, where $R_1$, n, $R_2$ and $R_3$ have the meaning as defined above, is reacted with an amine of the formula V where A and B have the meaning as defined above, optionally in the presence of a base and optionally in the presence of a diluting agent.

Any carboxy-activated derivatives are suitable as carboxy-activated derivatives of the amino acid of formula II, such as acid halides, for example acid chlorides or fluorides; symmetrical or mixed anhydrides, for example the mixed O-alkylcarboxylic acid anhydrides; activated esters, for example p-nitrophenyl esters or N-hydroxysuccinimide esters, and activated forms of the amino acid II produced in situ using condensation agents (e.g.

b)

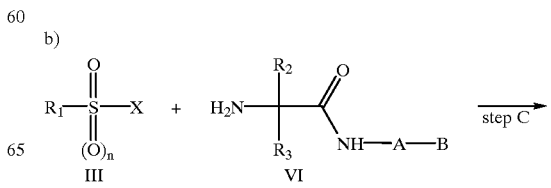

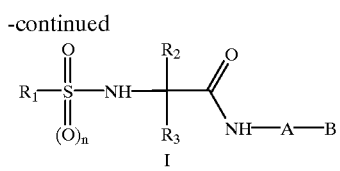

Step C: The compounds of formula I can also be prepared by reaction of an amino acid derivative of formula VI where $R_2$, $R_3$, A and B have the same meanings as defined above with a sulfonyl halide or a sulfinyl halide of formula III where $R_1$ and n have the same meanings as defined above and where X is halide, preferentially chlorine or bromine. The reaction is performed in the same manner as described for step A.

c) The compounds of the formula I, wherein n is 1 can be prepared by oxidizing compounds of formula I wherein n=0 (I') with organic oxidizing agents, such as alkyl hydroperoxides, for example cumyl hydroperoxide, and inorganic oxidizing agents, such as peroxides, for example hydrogen peroxide, or transition metal oxides, for example chromium trioxide, and transition metal oxide salts, for example potassium permanganate, potassium or sodium dichromate, are suitable oxidizing agents.

The reaction of the compounds of formula I' with the oxidizing agents takes place in an inert diluent, such as water or a ketone, for example acetone, or in mixtures thereof, in the absence or presence of an acid or in the absence or presence of a base, at temperatures of from −80 to +150° C.

The compounds of formula VI can be prepared by the following process d)

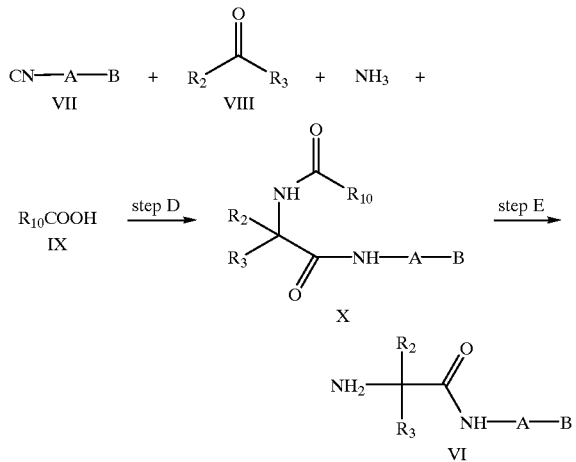

Step D: An isocyanide of formula VII, where A and B are as defined before (see D.Seebach, G.Adam, T.Gees, M.Schiess, W.Weigang, Chem.Ber.,1988,121,507) is reacted with a known compound of formula VIII ($R_2$ and $R_3$ are as defined before), a known compound of formula IX ($R_{10}$ is lower alkyl or H) and ammonia in a solvent (typically an alcohol as methanol or ethanol, tetrahydrofuran, methylenchloride) at a temperature between −20° and +150° C., optionally in the presence of a Lewis acid, typically $ZnCl_2$ (Ugi reaction).

Step E: A compound of formula X, where $R_2$, $R_3$, $R_{10}$, A and B are as defined before, is hydrolysed under acidic or basic conditions at a temperature between 0° and 100° C. Typical acids are mineral acids as HCl, $H_2SO_4$, organic acids as p-toluenesulfonic acid, methanesulfonic acid, trifluoroacetic acid; typical bases are NaOH, KOH, $Ba(OH)_2$, carbonates, triethylamine, ethyl diisopropylamine; typical solvents are alcohols like ethanol or methanol, tetrahydrofurane, dimethylformamide, dimethylsulfoxide.

Compound VI can be converted to compounds of formula I by step C as described under process b).

The invention relates also to the amino acid derivatives of formula VI, wherein $R_2$, $R_3$, A and B have the meaning as defined for formula I.

The sulfonic acid or sulfinic acid or the sulfonic or sulfinic acid derivative of formula III required for process a) or b) and the amino acids of formula IV required for process a) are known per se.

Suitable sulfonic or sulfinic acid derivatives of formula III are any compounds wherein Z is a leaving group, such as sulfonic acid halides or sulfinic acid halides, e.g. sulfochlorides or sulfinic acid chlorides; symmetrical or mixed anhydrides; and activated forms of sulfonic acid or sulfinic acid produced in situ using condensation agents, such as dicyclohexylcarbodiimide or carbonyldiimidazole.

Surprisingly, it has now been found that compounds of formula I have for practical purposes a very advantageous biocidal spectrum in the control of phytopathogenic microorganisms, especially fungi. They possess very advantageous curative and preventive properties and are used in the protection of numerous crop plants. With the compounds of formula I it is possible to inhibit or destroy pests occurring on various crops of useful plants or on parts of such plants (fruit, blossom, leaves, stems, tubers, roots), while parts of the plants which grow later, for example, also remain protected against phytopathogenic fungi. The novel compounds of formula I prove to be preferentially effective against specific genera of the fungus class Fungi imperfecti (e.g. Cercospora), Basidiomycetes (e.g. Puccinia) and Ascomycetes (e.g. Erysiphe and Venturia) and especially against Oomycetes (e.g. Plasmopara, Peronospora, Bremia, Pythium, Phytophthora). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredients, especially plant-protecting compositions, and to the use thereof in the agricultural sector or related fields.

In addition, the present invention includes the preparation of those compositions, wherein the active ingredient is homogeneously mixed with one or more of the substances or groups of substances herein described. Also included is a method for the treatment of plants which comprises applying the novel compounds of formula I or the novel compositions.

Target crops to be protected within the scope of this invention comprise, for example, the following species of plants: cereals (wheat, barley, rye, oats, rice, maize, sorghum, spelt, triticale and related species); beet (sugar beet and fodder beet); pomes, stone fruit and soft fruit (apples, pears, plums, peaches, almonds, cherries, strawberries, raspberries and blackberries); leguminous plants (beans, lentils, peas and soybeans); oil plants (rape, mustard, poppy, olives, sunflowers, coconut, castor oil plants, cocoa beans and ground-nuts); cucumber plants (marrows, cucumbers and melons); fibre plants (cotton, flax, hemp and jute); citrus fruit (oranges, lemons, grapefruit and mandarins); vegetables (spinach, lettuce, asparagus, cabbages, carrots, onions, tomatoes, potatoes and paprika); lauraceae (avocados, cinnamon and camphor) and plants such as tobacco, nuts, coffee, sugar cane, tea, pepper, vines, hops, bananas and natural rubber plants, and also ornamentals.

The compounds of formula I are normally applied in the form of compositions and can be applied to the area or plant to be treated simultaneously or in succession with further active ingredients. Those further active ingredients may be fertilizers, micronutrient donors or other preparations that influence plant growth. It is also possible to use selective herbicides, and insecticides, fungicides, bactericides, nematicides, molluscicides or mixtures of several of those preparations, if desired together with further carriers, surfactants or other application-promoting adjuvants customarily employed in formulation technology.

Suitable carriers and adjuvants may be solid or liquid and correspond to the substances ordinarily employed in formulation technology, such as, e.g. natural or regenerated mineral substances, solvents, dispersants, wetting agents, tackifiers, thickeners, binding agents or fertilizers. Such carriers are for example described in WO 97/33890.

A preferred method of applying a compound of formula I, or an agrochemical composition comprising at least one of those compounds, is application to the foliage of the plants (foliar application), the frequency and the rate of application depending upon the risk of infestation by the pathogen in question. The compounds of formula I may also be applied to propagation material (grains, fruits, tubers, shoots, cuttings, roots etc.) (dressing), for example either by impregnating cereal grains (seeds) or potato tubers or freshly cut shoots with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and also encapsulations in e.g. polymer substances. As with the nature of the compositions, the methods of application, such as spraying, atomizing, dusting, scattering, coating or pouring, are chosen in accordance with the intended objectives and the prevailing circumstances.

Advantageous rates of application are normally from 1 g to 2 kg of active ingredient (a.i.) per hectare, preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the compound (active ingredient) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

The compounds of formula I can be mixed with other fungicides, resulting in some cases in unexpected synergistic activities. Mixing components which are particularly preferred are azoles such as azaconazole, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, tebuconazole, tetraconazole, triadimefon, triadimenol, triflumizole or triticonazole; pyrimidinyl carbinoles such as ancymidol, fenarimol or nuacompol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, mepanipyrim or pyrimethanil; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodione, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, 2-[(2-trifluoromethyl)-pyrid-6-yloxymethyl]-3-methoxyacrylate or 2-[α{[(α-methyl-3-trifluoromethyl-benzyl)imino]-oxy}-o-tolyl]-glyoxylic acid-methylester-O-methyloxime; dithiocarbamates such as ferbam, mancozeb, maneb, metiram, propineb, thiram, zineb or ziram; N-halomethylthiodicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or tolcofos-methyl; and other compounds of diverse structures such as acibenzolar-S-methyl, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine or validamycin.

The agrochemical compositions usually comprise 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The Examples which follow illustrate the invention described above, without limiting the scope thereof in any way. Temperatures are given in degrees Celsius.

TABLE 1

Compounds of formula I.1

(I.1)

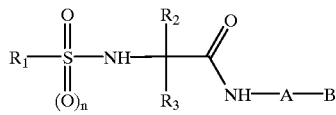

wherein R$_1$ is methyl and n is the number one and where the combination of R$_2$, R$_3$, A and B corresponds to one line in Table A.

TABLE 2

Compounds of formula I.1 wherein $R_1$ is ethyl and n is the number one and where the combination of
$R_2$, $R_3$, A and B corresponds to one line in Table A.

TABLE 3

Compounds of formula I.1 wherein $R_1$ is ethyl and n is zero and where the combination of $R_2$, $R_3$, A and B corresponds to one line in Table A.

TABLE 4

Compounds of formula I.1 wherein $R_1$ is propyl and n is the number one and where the combination of $R_2$, $R_3$, A and B corresponds to one line in Table A.

TABLE 5

Compounds of formula I.1 wherein $R_1$ is propyl and n is zero and where the combination of $R_2$, $R_3$, A and B corresponds to one line in Table A.

TABLE 6

Compounds of formula I.1 wherein $R_1$ is isopropyl and n is the number one and where the combination of $R_2$, $R_3$, A and B corresponds to one line in Table A.

TABLE 7

Compounds of formula I.1 wherein $R_1$ is isopropyl and n is zero and where the combination of $R_2$, $R_3$, A and B corresponds to one line in Table A.

TABLE 8

Compounds of formula I.1 wherein $R_1$ is butyl and n is the number one and where the combination of
$R_2$, $R_3$, A and B corresponds to one line in Table A.

TABLE 9

Compounds of formula I.1 wherein $R_1$ is butyl and n is zero and where the combination of $R_2$, $R_3$, A and B corresponds to one line in Table A.

TABLE 10

Compounds of formula I.1 wherein $R_1$ is 3-chloro-propyl and n is the number one and where the combination of $R_2$, $R_3$, A and B corresponds to one line in Table A.

TABLE 11

Compounds of formula I.1 wherein $R_1$ is dimethylamino and n is the number one and where the combination of $R_2$, $R_3$, A and B corresponds to one line in Table A.

TABLE 12

Compounds of formula I.1 wherein $R_1$ is phenyl and n is the number one and where the combination of $R_2$, $R_3$, A and B corresponds to one line in Table A.

TABLE 13

Compounds of formula I.1 wherein $R_1$ is benzyl and n is the number one and where the combination of $R_2$, $R_3$, A and B corresponds to one line in Table A.

TABLE 14

Compounds of formula I.2

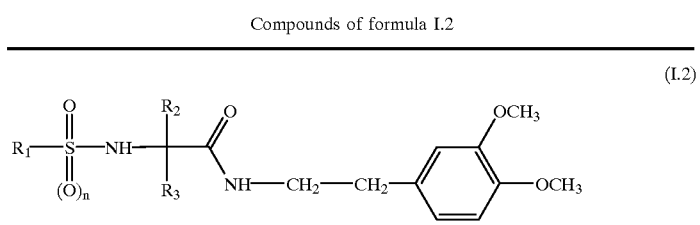

(I.2)

wherein $R_2$ is hydrogen and where the combination of $R_1$, $R_3$ and n corresponds to one line in Table B.

TABLE 15

Compounds of formula I.3

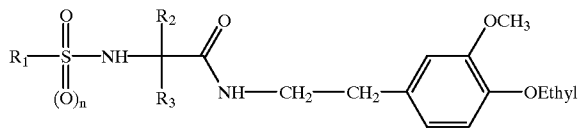
(I.3)

wherein $R_2$ is hydrogen and where the combination of $R_1$, $R_3$ and n corresponds to one line in Table B.

TABLE 16

Compounds of formula I.4

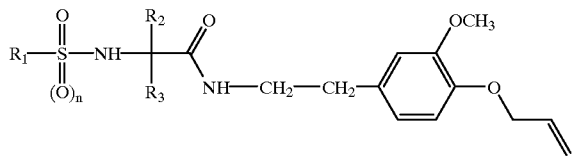
(I.4)

wherein $R_2$ is hydrogen and where the combination of $R_1$, $R_3$ and n corresponds to one line in Table B.

TABLE 17

Compounds of formula I.5

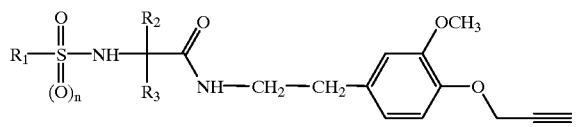
(I.5)

wherein $R_2$ is hydrogen and where the combination of $R_1$, $R_3$ and n corresponds to one line in Table B.

TABLE 18

Compounds of formula I.6

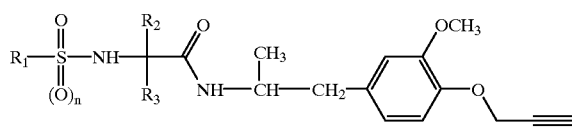
(I.6)

wherein $R_2$ is hydrogen and where the combination of $R_1$, $R_3$ and n corresponds to one line in Table B.

TABLE 19

Compounds of formula I.7

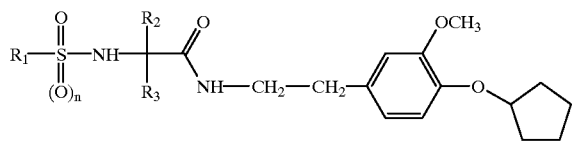
(I.7)

wherein $R_2$ is hydrogen and where the combination of $R_1$, $R_3$ and n corresponds to one line in Table B.

15

TABLE 20

Compounds of formula I.8

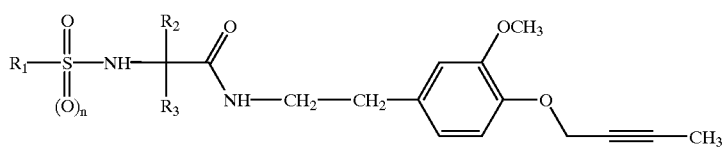
(I.8)

wherein $R_2$ is hydrogen and where the combination of $R_1$, $R_3$ and n corresponds to one line in Table B.

TABLE 21

Compounds of formula I.9

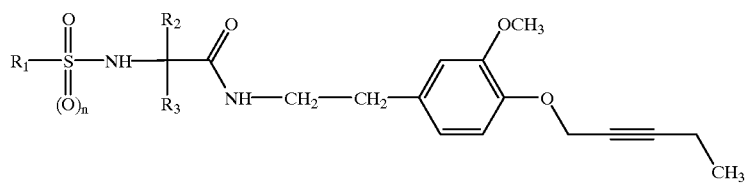
(I.9)

wherein $R_2$ is hydrogen and where the combination of $R_1$, $R_3$ and n corresponds to one line in Table B.

TABLE 22

Compounds of formula I.10

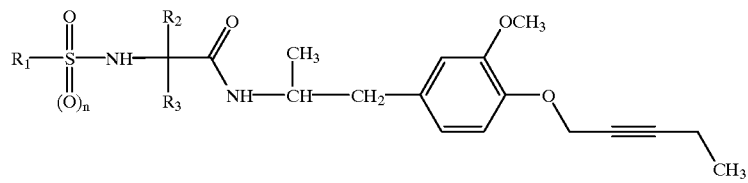
(I.10)

wherein $R_2$ is hydrogen and where the combination of $R_1$, $R_3$ and n corresponds to one line in Table B.

TABLE 23

Compounds of formula I.11

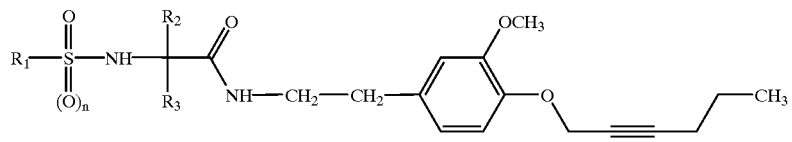

(I.11)

wherein $R_2$ is hydrogen and where the combination of $R_1$, $R_3$ and n corresponds to one line in Table B.

TABLE 24

Compounds of formula I.12

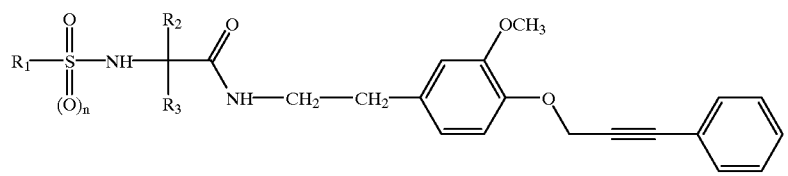

(I.12)

wherein $R_2$ is hydrogen and where the combination of $R_1$, $R_3$ and n corresponds to one line in Table B.

TABLE 25

Compounds of formula I.13

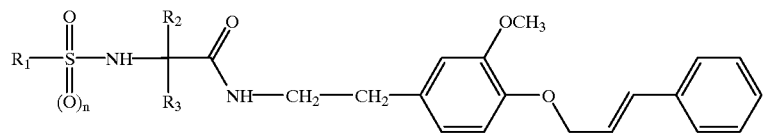

(I.13)

wherein $R_2$ is hydrogen and where the combination of $R_1$, $R_3$ and n corresponds to one line in Table B.

TABLE 26

Compounds of formula I.14

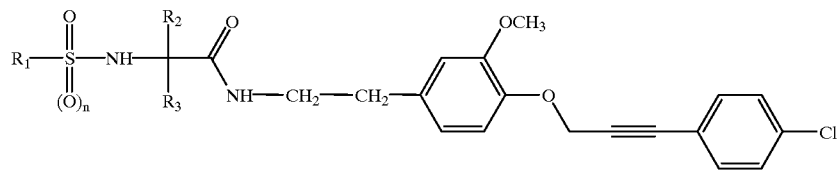

(I.14)

wherein $R_2$ is hydrogen and where the combination of $R_1$, $R_3$ and n corresponds to one line in Table B.

TABLE 27

Compounds of formula I.15

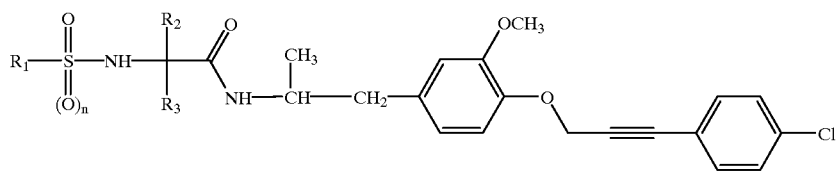
(I.15)

wherein R₂ is hydrogen and where the combination of $R_1$, $R_3$ and n corresponds to one line in Table B.

TABLE 28

Compounds of formula I.16

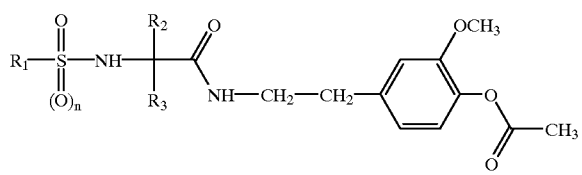
(I.16)

wherein R₂ is hydrogen and where the combination of $R_1$, $R_3$ and n corresponds to one line in Table B

TABLE 29

Compounds of formula I.17

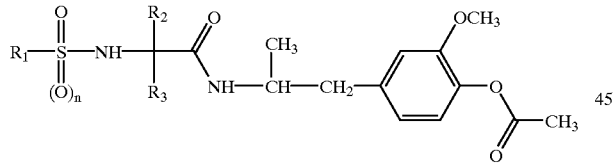
(I.17)

wherein R₂ is hydrogen and where the combination of $R_1$, $R_3$ and n corresponds to one line in Table B

TABLE 30

Compounds of formula I.18

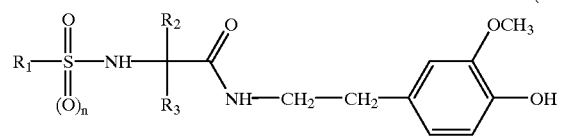
(I.18)

wherein R₂ is hydrogen and where the combination of $R_1$, $R_3$ and n corresponds to one line in Table B

TABLE 31

Compounds of formula I.19

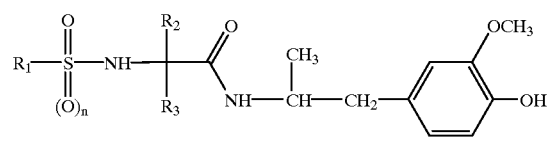
(I.19)

wherein R₂ is hydrogen and where the combination of $R_1$, $R_3$ and n corresponds to one line in Table B

TABLE 32

Compounds of formula I.20

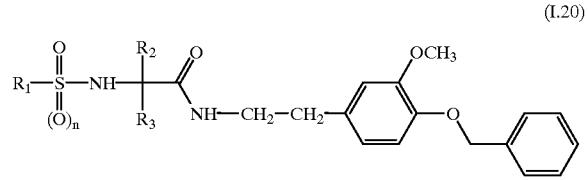
(I.20)

wherein R₂ is hydrogen and where the combination of $R_1$, $R_3$ and n corresponds to one line in Table B

TABLE 33

Compounds of formula I.21

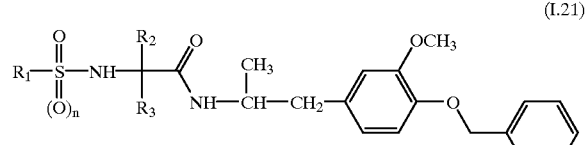
(I.21)

wherein R₂ is hydrogen and where the combination of $R_1$, $R_3$ and n corresponds to one line in Table B

TABLE 34

Compounds of formula I.22

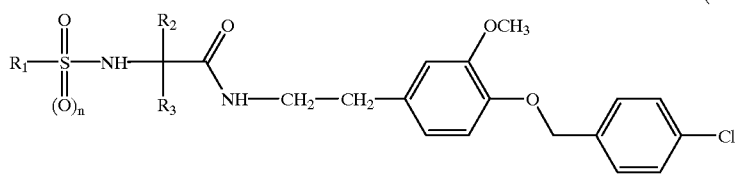

(I.22)

wherein $R_2$ is hydrogen and where the combination of $R_1$, $R_3$ and n corresponds to one line in Table B

TABLE 35

Compounds of formula I.23

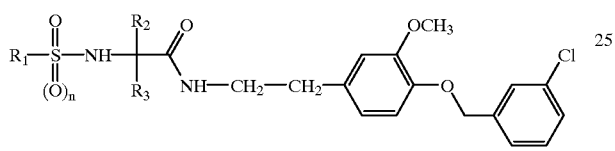

(I.23)

wherein $R_2$ is hydrogen and where the combination of $R_1$, $R_3$ and n corresponds to one line in Table B

TABLE 36

Compounds of formula I.24

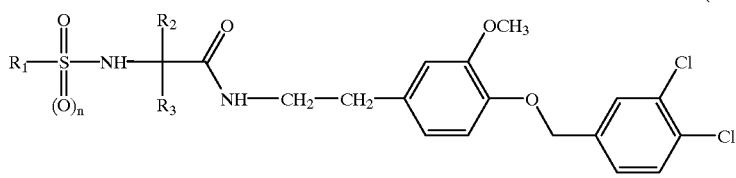

(I.24)

wherein $R_2$ is hydrogen and where the combination of $R_1$, $R_3$ and n corresponds to one line in Table B

TABLE 37

Compounds of formula I.25

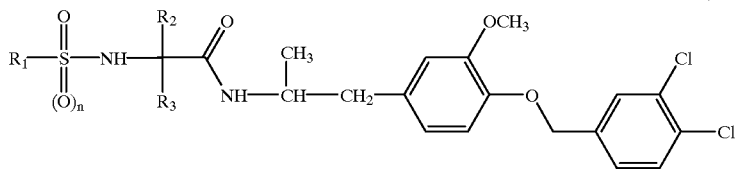

(I.25)

wherein $R_2$ is hydrogen and where the combination of $R_1$, $R_3$ and n corresponds to one line in Table B

TABLE 38

Compounds of formula I.26

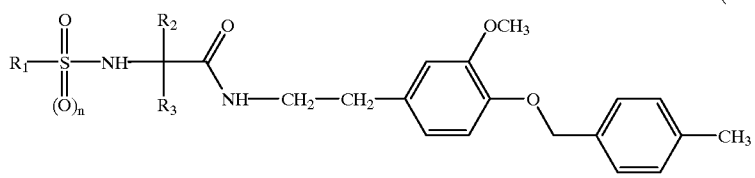

(I.26)

wherein $R_2$ is hydrogen and where the combination of $R_1$, $R_3$ and n corresponds to one line in Table B

TABLE 39

Compounds of formula I.27

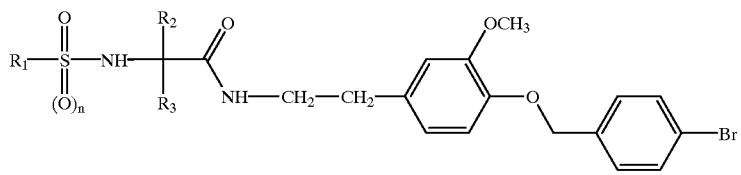

(I.27)

wherein $R_2$ is hydrogen and where the combination of $R_1$, $R_3$ and n corresponds to one line in Table B

TABLE 40

Compounds of formula I.28

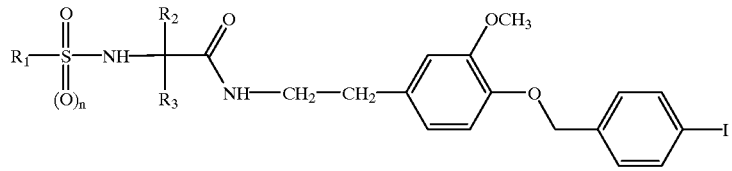

(I.28)

wherein $R_2$ is hydrogen and where the combination of $R_1$, $R_3$ and n corresponds to one line in Table B

TABLE 41

Compounds of formula I.29

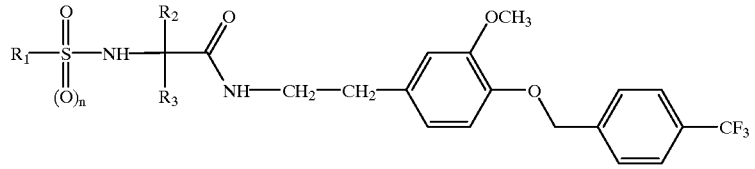

(I.29)

wherein $R_2$ is hydrogen and where the combination of $R_1$, $R_3$ and n corresponds to one line in Table B

TABLE 42

Compounds of formula I.30

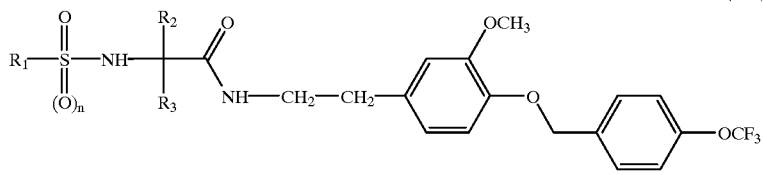

(I.30)

wherein $R_2$ is hydrogen and where the combination of $R_1$, $R_3$ and n corresponds to one line in Table B

TABLE 43

Compounds of formula I.31

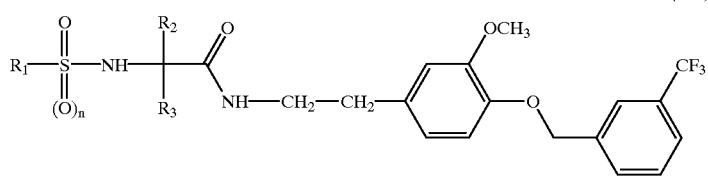

(I.31)

wherein $R_2$ is hydrogen and where the combination of $R_1$, $R_3$ and n corresponds to one line in Table B

TABLE 44

Compounds of formula I.32

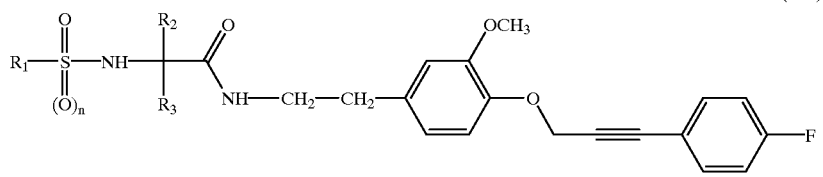

(I.32)

wherein $R_2$ is hydrogen and where the combination of $R_1$, $R_3$ and n corresponds to one line in Table B

TABLE 45

Compounds of formula I.33

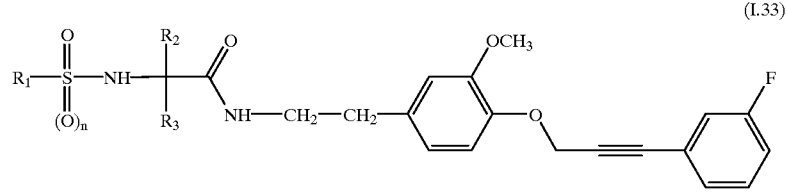

(I.33)

wherein $R_2$ is hydrogen and where the combination of $R_1$, $R_3$ and n corresponds to one line in Table B

TABLE 46

Compounds of formula I.34

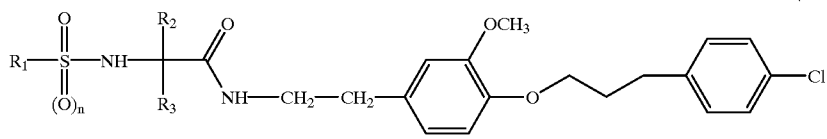
(I.34)

wherein $R_2$ is hydrogen and where the combination of $R_1$, $R_3$ and n corresponds to one line in Table B

TABLE 47

Compounds of formula I.35

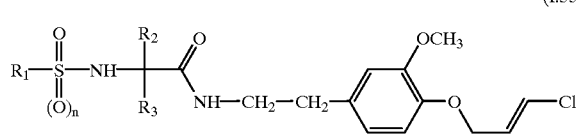
(I.35)

wherein $R_2$ is hydrogen and where the combination of $R_1$, $R_3$ and n corresponds to one line in Table B

TABLE 48

Compounds of formula I.36

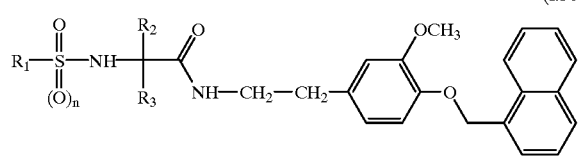
(I.36)

wherein $R_2$ is hydrogen and where the combination of $R_1$, $R_3$ and n corresponds to one line in Table B

TABLE 49

Compounds of formula I.37

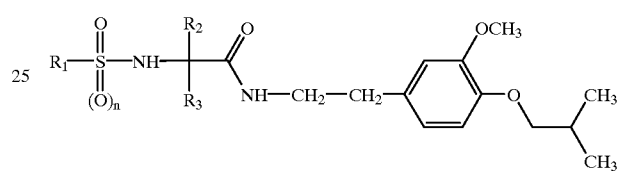
(I.37)

wherein $R_2$ is hydrogen and where the combination of $R_1$, $R_3$ and n corresponds to one line in Table B

TABLE 50

Compounds of formula I.38

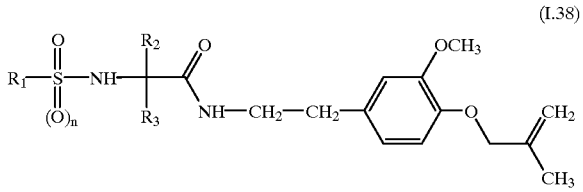
(I.38)

wherein $R_2$ is hydrogen and where the combination of $R_1$, $R_3$ and n corresponds to one line in Table B

TABLE A (wherein Et means ethyl and c. means cyclo)

| No.  | $R_2$ | $R_3$  | A       | B                         |
|------|-------|--------|---------|---------------------------|
| A.1  | H     | phenyl | —$CH_2$— | phenyl                    |
| A.2  | H     | phenyl | —$CH_2$— | 4-Cl-phenyl               |
| A.3  | H     | phenyl | —$CH_2$— | 3,4-di-Cl-phenyl          |
| A.4  | H     | phenyl | —$CH_2$— | 2,4-di-Cl-phenyl          |
| A.5  | H     | phenyl | —$CH_2$— | 4-Br-phenyl               |
| A.6  | H     | phenyl | —$CH_2$— | 4-$CH_3$-phenyl           |
| A.7  | H     | phenyl | —$CH_2$— | 4-Et-phenyl               |
| A.8  | H     | phenyl | —$CH_2$— | 4-$OCH_3$-phenyl          |
| A.9  | H     | phenyl | —$CH_2$— | 4-$CF_3$-phenyl           |
| A.10 | H     | phenyl | —$CH_2$— | 4-c.$C_5H_9$-phenyl       |
| A.11 | H     | phenyl | —$CH_2$— | 3-$OCH_3$-4-phenoxy-phenyl |
| A.12 | H     | phenyl | —$CH_2$— | 3-$OCH_3$-4-$SCH_3$-phenyl |

TABLE A-continued (wherein Et means ethyl and c. means cyclo)

| No. | $R_2$ | $R_3$ | A | B |
|---|---|---|---|---|
| A.13 | H | phenyl | —CH$_2$— | 4-CH$_3$OOC-phenyl |
| A.14 | H | phenyl | —CH$_2$— | 3-NO$_2$-phenyl |
| A.15 | H | phenyl | —CH$_2$— | 4-CN-phenyl |
| A.16 | H | phenyl | —CH$_2$— | 4-N(CH$_3$)$_2$-phenyl |
| A.17 | H | phenyl | —CH(CH$_3$)— | phenyl |
| A.18 | H | phenyl | —CH(CH$_3$)— | 4-Cl-phenyl |
| A.19 | H | phenyl | —CH(CH$_3$)— | 3,4-di-Cl-phenyl |
| A.20 | H | phenyl | —CH(CH$_3$)— | 2,4-di-Cl-phenyl |
| A.21 | H | phenyl | —CH(CH$_3$)— | 4-Br-phenyl |
| A.22 | H | phenyl | —CH(CH$_3$)— | 4-CH$_3$-phenyl |
| A.23 | H | phenyl | —CH(CH$_3$)— | 4-Et-phenyl |
| A.24 | H | phenyl | —CH(CH$_3$)— | 4-OCH$_3$-phenyl |
| A.25 | H | phenyl | —CH(CH$_3$)— | 4-CF$_3$-phenyl |
| A.26 | H | phenyl | —CH(CH$_3$)— | 4-c.C$_5$H$_9$-phenyl |
| A.27 | H | phenyl | —CH(CH$_3$)— | 3-OCH$_3$-4-phenoxy-phenyl |
| A.28 | H | phenyl | —CH(CH$_3$)— | 3-OCH$_3$-4-SCH$_3$-phenyl |
| A.29 | H | phenyl | —CH(CH$_3$)— | 4-CH$_3$OOC-phenyl |
| A.30 | H | phenyl | —CH(CH$_3$)— | 3-NO$_2$-phenyl |
| A.31 | H | phenyl | —CH(CH$_3$)— | 4-CN-phenyl |
| A.32 | H | phenyl | —CH(CH$_3$)— | 4-N(CH$_3$)$_2$-phenyl |
| A.33 | H | phenyl | —CH$_2$CH$_2$— | phenyl |
| A.34 | H | phenyl | —CH$_2$CH$_2$— | 4-Cl-phenyl |
| A.35 | H | phenyl | —CH$_2$CH$_2$— | 3,4-di-Cl-phenyl |
| A.36 | H | phenyl | —CH$_2$CH$_2$— | 2,4-di-Cl-phenyl |
| A.37 | H | phenyl | —CH$_2$CH$_2$— | 4-Br-phenyl |
| A.38 | H | phenyl | —CH$_2$CH$_2$— | 4-CH$_3$-phenyl |
| A.39 | H | phenyl | —CH$_2$CH$_2$— | 4-Et-phenyl |
| A.40 | H | phenyl | —CH$_2$CH$_2$— | 4-OCH$_3$-phenyl |
| A.41 | H | phenyl | —CH$_2$CH$_2$— | 4-CF$_3$-phenyl |
| A.42 | H | phenyl | —CH$_2$CH$_2$— | 4-c.C$_5$H$_9$-phenyl |
| A.43 | H | phenyl | —CH$_2$CH$_2$— | 3-OCH$_3$-4-phenoxy-phenyl |
| A.44 | H | phenyl | —CH$_2$CH$_2$— | 3-OCH$_3$-4-SCH$_3$-phenyl |
| A.45 | H | phenyl | —CH$_2$CH$_2$— | 4-CH$_3$OOC-phenyl |
| A.46 | H | phenyl | —CH$_2$CH$_2$— | 3-NO$_2$-phenyl |
| A.47 | H | phenyl | —CH$_2$CH$_2$— | 4-CN-phenyl |
| A.48 | H | phenyl | —CH$_2$CH$_2$— | 4-N(CH$_3$)$_2$-phenyl |
| A.49 | H | phenyl | —CH(CH$_3$)CH$_2$— | phenyl |
| A.50 | H | phenyl | —CH(CH$_3$)CH$_2$— | 4-Cl-phenyl |
| A.51 | H | phenyl | —CH(CH$_3$)CH$_2$— | 3,4-di-Cl-phenyl |
| A.52 | H | phenyl | —CH(CH$_3$)CH$_2$— | 2,4-di-Cl-phenyl |
| A.53 | H | phenyl | —CH(CH$_3$)CH$_2$— | 4-Br-phenyl |
| A.54 | H | phenyl | —CH(CH$_3$)CH$_2$— | 4-CH$_3$-phenyl |
| A.55 | H | phenyl | —CH(CH$_3$)CH$_2$— | 4-Et-phenyl |
| A.56 | H | phenyl | —CH(CH$_3$)CH$_2$— | 4-OCH$_3$-phenyl |
| A.57 | H | phenyl | —CH(CH$_3$)CH$_2$— | 4-CF$_3$-phenyl |
| A.58 | H | phenyl | —CH(CH$_3$)CH$_2$— | 4-c.C$_5$H$_9$-phenyl |
| A.59 | H | phenyl | —CH(CH$_3$)CH$_2$— | 3-OCH$_3$-4-phenoxy-phenyl |
| A.60 | H | phenyl | —CH(CH$_3$)CH$_2$— | 3-OCH$_3$-4-SCH$_3$-phenyl |
| A.61 | H | phenyl | —CH(CH$_3$)CH$_2$— | 4-CH$_3$OOC-phenyl |
| A.62 | H | phenyl | —CH(CH$_3$)CH$_2$— | 3-NO$_2$-phenyl |
| A.63 | H | phenyl | —CH(CH$_3$)CH$_2$— | 4-CN-phenyl |
| A.64 | H | phenyl | —CH(CH$_3$)CH$_2$— | 4-N(CH$_3$)$_2$-phenyl |
| A.65 | H | 4-Cl-phenyl | —CH$_2$— | phenyl |
| A.66 | H | 4-Cl-phenyl | —CH$_2$— | 4-Cl-phenyl |
| A.67 | H | 4-Cl-phenyl | —CH$_2$— | 3,4-di-Cl-phenyl |
| A.68 | H | 4-Cl-phenyl | —CH$_2$— | 2,4-di-Cl-phenyl |
| A.69 | H | 4-Cl-phenyl | —CH$_2$— | 4-Br-phenyl |
| A.70 | H | 4-Cl-phenyl | —CH$_2$— | 4-CH$_3$-phenyl |
| A.71 | H | 4-Cl-phenyl | —CH$_2$— | 4-Et-phenyl |
| A.72 | H | 4-Cl-phenyl | —CH$_2$— | 4-OCH$_3$-phenyl |
| A.73 | H | 4-Cl-phenyl | —CH$_2$— | 4-CF$_3$-phenyl |
| A.74 | H | 4-Cl-phenyl | —CH$_2$— | 4-c.C$_5$H$_9$-phenyl |
| A.75 | H | 4-Cl-phenyl | —CH$_2$— | 3-OCH$_3$-4-phenoxy-phenyl |
| A.76 | H | 4-Cl-phenyl | —CH$_2$— | 3-OCH$_3$-4-SCH$_3$-phenyl |
| A.77 | H | 4-Cl-phenyl | —CH$_2$— | 4-CH$_3$OOC-phenyl |
| A.78 | H | 4-Cl-phenyl | —CH$_2$— | 3-NO$_2$-phenyl |
| A.79 | H | 4-Cl-phenyl | —CH$_2$— | 4-CN-phenyl |
| A.80 | H | 4-Cl-phenyl | —CH$_2$— | 4-N(CH$_3$)$_2$-phenyl |
| A.81 | H | 4-Cl-phenyl | —CH(CH$_3$)— | phenyl |
| A.82 | H | 4-Cl-phenyl | —CH(CH$_3$)— | 4-Cl-phenyl |
| A.83 | H | 4-Cl-phenyl | —CH(CH$_3$)— | 3,4-di-Cl-phenyl |
| A.84 | H | 4-Cl-phenyl | —CH(CH$_3$)— | 2,4-di-Cl-phenyl |
| A.85 | H | 4-Cl-phenyl | —CH(CH$_3$)— | 4-Br-phenyl |
| A.86 | H | 4-Cl-phenyl | —CH(CH$_3$)— | 4-CH$_3$-phenyl |
| A.87 | H | 4-Cl-phenyl | —CH(CH$_3$)— | 4-Et-phenyl |

TABLE A-continued (wherein Et means ethyl and c. means cyclo)

| No. | R$_2$ | R$_3$ | A | B |
|---|---|---|---|---|
| A.88 | H | 4-Cl-phenyl | —CH(CH$_3$)— | 4-OCH$_3$-phenyl |
| A.89 | H | 4-Cl-phenyl | —CH(CH$_3$)— | 4-CF$_3$-phenyl |
| A.90 | H | 4-Cl-phenyl | —CH(CH$_3$)— | 4-c.C$_5$H$_9$-phenyl |
| A.91 | H | 4-Cl-phenyl | —CH(CH$_3$)— | 3-OCH$_3$-4-phenoxy-phenyl |
| A.92 | H | 4-Cl-phenyl | —CH(CH$_3$)— | 3-OCH$_3$-4-SCH$_3$-phenyl |
| A.93 | H | 4-Cl-phenyl | —CH(CH$_3$)— | 4-CH$_3$OOC-phenyl |
| A.94 | H | 4-Cl-phenyl | —CH(CH$_3$)— | 3-NO$_2$-phenyl |
| A.95 | H | 4-Cl-phenyl | —CH(CH$_3$)— | 4-CN-phenyl |
| A.96 | H | 4-Cl-phenyl | —CH(CH$_3$)— | 4-N(CH$_3$)$_2$-phenyl |
| A.97 | H | 4-Cl-phenyl | —CH$_2$CH$_2$— | phenyl |
| A.98 | H | 4-Cl-phenyl | —CH$_2$CH$_2$— | 4-Cl-phenyl |
| A.99 | H | 4-Cl-phenyl | —CH$_2$CH$_2$— | 3,4-di-Cl-phenyl |
| A.100 | H | 4-Cl-phenyl | —CH$_2$CH$_2$— | 2,4-di-Cl-phenyl |
| A.101 | H | 4-Cl-phenyl | —CH$_2$CH$_2$— | 4-Br-phenyl |
| A.102 | H | 4-Cl-phenyl | —CH$_2$CH$_2$— | 4-CH$_3$-phenyl |
| A.103 | H | 4-Cl-phenyl | —CH$_2$CH$_2$— | 4-Et-phenyl |
| A.104 | H | 4-Cl-phenyl | —CH$_2$CH$_2$— | 4-OCH$_3$-phenyl |
| A.105 | H | 4-Cl-phenyl | —CH$_2$CH$_2$— | 4-CF$_3$-phenyl |
| A.106 | H | 4-Cl-phenyl | —CH$_2$CH$_2$— | 4-c.C$_5$H$_9$-phenyl |
| A.107 | H | 4-Cl-phenyl | —CH$_2$CH$_2$— | 3-OCH$_3$-4-phenoxy-phenyl |
| A.108 | H | 4-Cl-phenyl | —CH$_2$CH$_2$— | 3-OCH$_3$-4-SCH$_3$-phenyl |
| A.109 | H | 4-Cl-phenyl | —CH$_2$CH$_2$— | 4-CH$_3$OOC-phenyl |
| A.110 | H | 4-Cl-phenyl | —CH$_2$CH$_2$— | 3-NO$_2$-phenyl |
| A.111 | H | 4-Cl-phenyl | —CH$_2$CH$_2$— | 4-CN-phenyl |
| A.112 | H | 4-Cl-phenyl | —CH$_2$CH$_2$— | 4-N(CH$_3$)$_2$-phenyl |
| A.113 | H | 4-Cl-phenyl | —CH(CH$_3$)CH$_2$— | phenyl |
| A.114 | H | 4-Cl-phenyl | —CH(CH$_3$)CH$_2$— | 4-Cl-phenyl |
| A.115 | H | 4-Cl-phenyl | —CH(CH$_3$)CH$_2$— | 3,4-di-Cl-phenyl |
| A.116 | H | 4-Cl-phenyl | —CH(CH$_3$)CH$_2$— | 2,4-di-Cl-phenyl |
| A.117 | H | 4-Cl-phenyl | —CH(CH$_3$)CH$_2$— | 4-Br-phenyl |
| A.118 | H | 4-Cl-phenyl | —CH(CH$_3$)CH$_2$— | 4-CH$_3$-phenyl |
| A.119 | H | 4-Cl-phenyl | —CH(CH$_3$)CH$_2$— | 4-Et-phenyl |
| A.120 | H | 4-Cl-phenyl | —CH(CH$_3$)CH$_2$— | 4-OCH$_3$-phenyl |
| A.121 | H | 4-Cl-phenyl | —CH(CH$_3$)CH$_2$— | 4-CF$_3$-phenyl |
| A.122 | H | 4-Cl-phenyl | —CH(CH$_3$)CH$_2$— | 4-c.C$_5$H$_9$-phenyl |
| A.123 | H | 4-Cl-phenyl | —CH(CH$_3$)CH$_2$— | 3-OCH$_3$-4-phenoxy-phenyl |
| A.124 | H | 4-Cl-phenyl | —CH(CH$_3$)CH$_2$— | 3-OCH$_3$-4-SCH$_3$-phenyl |
| A.125 | H | 4-Cl-phenyl | —CH(CH$_3$)CH$_2$— | 4-CH$_3$OOC-phenyl |
| A.126 | H | 4-Cl-phenyl | —CH(CH$_3$)CH$_2$— | 3-NO$_2$-phenyl |
| A.127 | H | 4-Cl-phenyl | —CH(CH$_3$)CH$_2$— | 4-CN-phenyl |
| A.128 | H | 4-Cl-phenyl | —CH(CH$_3$)CH$_2$— | 4-N(CH$_3$)$_2$-phenyl |
| A.129 | H | 3,4-di-Cl-phenyl | —CH$_2$— | phenyl |
| A.130 | H | 3,4-di-Cl-phenyl | —CH$_2$— | 4-Cl-phenyl |
| A.131 | H | 3,4-di-Cl-phenyl | —CH$_2$— | 3,4-di-Cl-phenyl |
| A.132 | H | 3,4-di-Cl-phenyl | —CH$_2$— | 2,4-di-Cl-phenyl |
| A.133 | H | 3,4-di-Cl-phenyl | —CH$_2$— | 4-Br-phenyl |
| A.134 | H | 3,4-di-Cl-phenyl | —CH$_2$— | 4-CH$_3$-phenyl |
| A.135 | H | 3,4-di-Cl-phenyl | —CH$_2$— | 4-Et-phenyl |
| A.136 | H | 3,4-di-Cl-phenyl | —CH$_2$— | 4-OCH$_3$-phenyl |
| A.137 | H | 3,4-di-Cl-phenyl | —CH$_2$— | 4-CF$_3$-phenyl |
| A.138 | H | 3,4-di-Cl-phenyl | —CH$_2$— | 4-c.C$_5$H$_9$-phenyl |
| A.139 | H | 3,4-di-Cl-phenyl | —CH$_2$— | 3-OCH$_3$-4-phenoxy-phenyl |
| A.140 | H | 3,4-di-Cl-phenyl | —CH$_2$— | 3-OCH$_3$-4-SCH$_3$-phenyl |
| A.141 | H | 3,4-di-Cl-phenyl | —CH$_2$— | 4-CH$_3$OOC-phenyl |
| A.142 | H | 3,4-di-Cl-phenyl | —CH$_2$— | 3-NO$_2$-phenyl |
| A.143 | H | 3,4-di-Cl-phenyl | —CH$_2$— | 4-CN-phenyl |
| A.144 | H | 3,4-di-Cl-phenyl | —CH$_2$— | 4-N(CH$_3$)$_2$-phenyl |
| A.145 | H | 3,4-di-Cl-phenyl | —CH(CH$_3$)— | phenyl |
| A.146 | H | 3,4-di-Cl-phenyl | —CH(CH$_3$)— | 4-Cl-phenyl |
| A.147 | H | 3,4-di-Cl-phenyl | —CH(CH$_3$)— | 3,4-di-Cl-phenyl |
| A.148 | H | 3,4-di-Cl-phenyl | —CH(CH$_3$)— | 2,4-di-Cl-phenyl |
| A.149 | H | 3,4-di-Cl-phenyl | —CH(CH$_3$)— | 4-Br-phenyl |
| A.150 | H | 3,4-di-Cl-phenyl | —CH(CH$_3$)— | 4-CH$_3$-phenyl |
| A.151 | H | 3,4-di-Cl-phenyl | —CH(CH$_3$)— | 4-Et-phenyl |
| A.152 | H | 3,4-di-Cl-phenyl | —CH(CH$_3$)— | 4-OCH$_3$-phenyl |
| A.153 | H | 3,4-di-Cl-phenyl | —CH(CH$_3$)— | 4-CF$_3$-phenyl |
| A.154 | H | 3,4-di-Cl-phenyl | —CH(CH$_3$)— | 4-c.C$_5$H$_9$-phenyl |
| A.155 | H | 3,4-di-Cl-phenyl | —CH(CH$_3$)— | 3-OCH$_3$-4-phenoxy-phenyl |
| A.156 | H | 3,4-di-Cl-phenyl | —CH(CH$_3$)— | 3-OCH$_3$-4-SCH$_3$-phenyl |
| A.157 | H | 3,4-di-Cl-phenyl | —CH(CH$_3$)— | 4-CH$_3$OOC-phenyl |
| A.158 | H | 3,4-di-Cl-phenyl | —CH(CH$_3$)— | 3-NO$_2$-phenyl |
| A.159 | H | 3,4-di-Cl-phenyl | —CH(CH$_3$)— | 4-CN-phenyl |
| A.160 | H | 3,4-di-Cl-phenyl | —CH(CH$_3$)— | 4-N(CH$_3$)$_2$-phenyl |
| A.161 | H | 3,4-di-Cl-phenyl | —CH$_2$CH$_2$— | phenyl |
| A.162 | H | 3,4-di-Cl-phenyl | —CH$_2$CH$_2$— | 4-Cl-phenyl |

TABLE A-continued (wherein Et means ethyl and c. means cyclo)

| No. | $R_2$ | $R_3$ | A | B |
|---|---|---|---|---|
| A.163 | H | 3,4-di-Cl-phenyl | —CH$_2$CH$_2$— | 3,4-di-Cl-phenyl |
| A.164 | H | 3,4-di-Cl-phenyl | —CH$_2$CH$_2$— | 2,4-di-Cl-phenyl |
| A.165 | H | 3,4-di-Cl-phenyl | —CH$_2$CH$_2$— | 4-Br-phenyl |
| A.166 | H | 3,4-di-Cl-phenyl | —CH$_2$CH$_2$— | 4-CH$_3$-phenyl |
| A.167 | H | 3,4-di-Cl-phenyl | —CH$_2$CH$_2$— | 4-Et-phenyl |
| A.168 | H | 3,4-di-Cl-phenyl | —CH$_2$CH$_2$— | 4-OCH$_3$-phenyl |
| A.169 | H | 3,4-di-Cl-phenyl | —CH$_2$CH$_2$— | 4-CF$_3$-phenyl |
| A.170 | H | 3,4-di-Cl-phenyl | —CH$_2$CH$_2$— | 4-c.C$_5$C$_9$-phenyl |
| A.171 | H | 3,4-di-Cl-phenyl | —CH$_2$CH$_2$— | 3-OCH$_3$-4-phenoxy-phenyl |
| A.172 | H | 3,4-di-Cl-phenyl | —CH$_2$CH$_2$— | 3-OCH$_3$-4-SCH$_3$-phenyl |
| A.173 | H | 3,4-di-Cl-phenyl | —CH$_2$CH$_2$— | 4-CH$_3$OOC-phenyl |
| A.174 | H | 3,4-di-Cl-phenyl | —CH$_2$CH$_2$— | 3-NO$_2$-phenyl |
| A.175 | H | 3,4-di-Cl-phenyl | —CH$_2$CH$_2$— | 4-CN-phenyl |
| A.176 | H | 3,4-di-Cl-phenyl | —CH$_2$CH$_2$— | 4-N(CH$_3$)$_2$-phenyl |
| A.177 | H | 3,4-di-Cl-phenyl | —CH(CH$_3$)CH$_2$— | phenyl |
| A.178 | H | 3,4-di-Cl-phenyl | —CH(CH$_3$)CH$_2$— | 4-Cl-phenyl |
| A.179 | H | 3,4-di-Cl-phenyl | —CH(CH$_3$)CH$_2$— | 3,4-di-Cl-phenyl |
| A.180 | H | 3,4-di-Cl-phenyl | —CH(CH$_3$)CH$_2$— | 2,4-di-Cl-phenyl |
| A.181 | H | 3,4-di-Cl-phenyl | —CH(CH$_3$)CH$_2$— | 4-Br-phenyl |
| A.182 | H | 3,4-di-Cl-phenyl | —CH(CH$_3$)CH$_2$— | 4-CH$_3$-phenyl |
| A.183 | H | 3,4-di-Cl-phenyl | —CH(CH$_3$)CH$_2$— | 4-Et-phenyl |
| A.184 | H | 3,4-di-Cl-phenyl | —CH(CH$_3$)CH$_2$— | 4-OCH$_3$-phenyl |
| A.185 | H | 3,4-di-Cl-phenyl | —CH(CH$_3$)CH$_2$— | 4-CF$_3$-phenyl |
| A.186 | H | 3,4-di-Cl-phenyl | —CH(CH$_3$)CH$_2$— | 4-c.C$_5$C$_9$-phenyl |
| A.187 | H | 3,4-di-Cl-phenyl | —CH(CH$_3$)CH$_2$— | 3-OCH$_3$-4-phenoxy-phenyl |
| A.188 | H | 3,4-di-Cl-phenyl | —CH(CH$_3$)CH$_2$— | 3-OCH$_3$-4-SCH$_3$-phenyl |
| A.189 | H | 3,4-di-Cl-phenyl | —CH(CH$_3$)CH$_2$— | 4-CH$_3$OOC-phenyl |
| A.190 | H | 3,4-di-Cl-phenyl | —CH(CH$_3$)CH$_2$— | 3-NO$_2$-phenyl |
| A.191 | H | 3,4-di-Cl-phenyl | —CH(CH$_3$)CH$_2$— | 4-CN-phenyl |
| A.192 | H | 3,4-di-Cl-phenyl | —CH(CH$_3$)CH$_2$— | 4-N(CH$_3$)$_2$-phenyl |
| A.193 | H | 4-Br-phenyl | —CH$_2$CH$_2$— | phenyl |
| A.194 | H | 4-Br-phenyl | —CH$_2$CH$_2$— | 4-Cl-phenyl |
| A.195 | H | 4-Br-phenyl | —CH$_2$CH$_2$— | 4-CH$_3$-phenyl |
| A.196 | H | 4-Br-phenyl | —CH$_2$CH$_2$— | 4-Et-phenyl |
| A.197 | H | 4-Br-phenyl | —CH$_2$CH$_2$— | 4-OCH$_3$-phenyl |
| A.198 | H | 4-Br-phenyl | —CH$_2$CH$_2$— | 3-OCH$_3$-4-phenoxy-phenyl |
| A.199 | H | 4-Br-phenyl | —CH$_2$CH$_2$— | 3-OCH$_3$-4-SCH$_3$-phenyl |
| A.200 | H | 4-Br-phenyl | —CH(CH$_3$)— | phenyl |
| A.201 | H | 4-Br-phenyl | —CH(CH$_3$)— | 4-Cl-phenyl |
| A.202 | H | 4-Br-phenyl | —CH(CH$_3$)— | 4-CH$_3$-phenyl |
| A.203 | H | 4-Br-phenyl | —CH(CH$_3$)— | 4-Et-phenyl |
| A.204 | H | 4-Br-phenyl | —CH(CH$_3$)— | 4-OCH$_3$-phenyl |
| A.205 | H | 4-Br-phenyl | —CH(CH$_3$)— | 3-OCH$_3$-4-phenoxy-phenyl |
| A.206 | H | 4-Br-phenyl | —CH(CH$_3$)— | 3-OCH$_3$-4-SCH$_3$-phenyl |
| A.207 | H | 4-CF$_3$-phenyl | —CH$_2$CH$_2$— | phenyl |
| A.208 | H | 4-CF$_3$-phenyl | —CH$_2$CH$_2$— | 4-Cl-phenyl |
| A.209 | H | 4-CF$_3$-phenyl | —CH$_2$CH$_2$— | 4-CH$_3$-phenyl |
| A.210 | H | 4-CF$_3$-phenyl | —CH$_2$CH$_2$— | 4-Et-phenyl |
| A.211 | H | 4-CF$_3$-phenyl | —CH$_2$CH$_2$— | 4-OCH$_3$-phenyl |
| A.212 | H | 4-CF$_3$-phenyl | —CH$_2$CH$_2$— | 3-OCH$_3$-4-phenoxy-phenyl |
| A.213 | H | 4-CF$_3$-phenyl | —CH$_2$CH$_2$— | 3-OCH$_3$-4-SCH$_3$-phenyl |
| A.214 | H | 4-CF$_3$-phenyl | —CH(CH$_3$)— | phenyl |
| A.215 | H | 4-CF$_3$-phenyl | —CH(CH$_3$)— | 4-Cl-phenyl |
| A.216 | H | 4-CF$_3$-phenyl | —CH(CH$_3$)— | 4-CH$_3$-phenyl |
| A.217 | H | 4-CF$_3$-phenyl | —CH(CH$_3$)— | 4-Et-phenyl |
| A.218 | H | 4-CF$_3$-phenyl | —CH(CH$_3$)— | 4-OCH$_3$-phenyl |
| A.219 | H | 4-CF$_3$-phenyl | —CH(CH$_3$)— | 3-OCH$_3$-4-phenoxy-phenyl |
| A.220 | H | 4-CF$_3$-phenyl | —CH(CH$_3$)— | 3-OCH$_3$-4-SCH$_3$-phenyl |
| A.221 | H | 4-CH$_3$-phenyl | —CH$_2$CH$_2$— | phenyl |
| A.222 | H | 4-CH$_3$-phenyl | —CH$_2$CH$_2$— | 4-Cl-phenyl |
| A.223 | H | 4-CH$_3$-phenyl | —CH$_2$CH$_2$— | 4-CH$_3$-phenyl |
| A.224 | H | 4-CH$_3$-phenyl | —CH$_2$CH$_2$— | 4-Et-phenyl |
| A.225 | H | 4-CH$_3$-phenyl | —CH$_2$CH$_2$— | 4-OCH$_3$-phenyl |
| A.226 | H | 4-CH$_3$-phenyl | —CH$_2$CH$_2$— | 3-OCH$_3$-4-phenoxy-phenyl |
| A.227 | H | 4-CH$_3$-phenyl | —CH$_2$CH$_2$— | 3-OCH$_3$-4-SCH$_3$-phenyl |
| A.228 | H | 4-CH$_3$-phenyl | —CH(CH$_3$)— | phenyl |
| A.229 | H | 4-CH$_3$-phenyl | —CH(CH$_3$)— | 4-Cl-phenyl |
| A.230 | H | 4-CH$_3$-phenyl | —CH(CH$_3$)— | 4-CH$_3$-phenyl |
| A.231 | H | 4-CH$_3$-phenyl | —CH(CH$_3$)— | 4-Et-phenyl |
| A.232 | H | 4-CH$_3$-phenyl | —CH(CH$_3$)— | 4-OCH$_3$-phenyl |
| A.233 | H | 4-CH$_3$-phenyl | —CH(CH$_3$)— | 3-OCH$_3$-4-phenoxy-phenyl |
| A.234 | H | 4-CH$_3$-phenyl | —CH(CH$_3$)— | 3-OCH$_3$-4-SCH$_3$-phenyl |
| A.235 | H | 4-F-phenyl | —CH$_2$CH$_2$— | 4-Cl-phenyl |
| A.236 | H | 4-F-phenyl | —CH$_2$CH$_2$— | 4-CH$_3$-phenyl |
| A.237 | H | 4-F-phenyl | —CH$_2$CH$_2$— | 4-OCH$_3$-phenyl |

TABLE A-continued (wherein Et means ethyl and c. means cyclo)

| No. | $R_2$ | $R_3$ | A | B |
|---|---|---|---|---|
| A.238 | H | 4-F-phenyl | —CH(CH$_3$)— | 4-Cl-phenyl |
| A.239 | H | 4-F-phenyl | —CH(CH$_3$)— | 4-CH$_3$-phenyl |
| A.240 | H | 4-F-phenyl | —CH(CH$_3$)— | 4-OCH$_3$-phenyl |
| A.241 | H | 4-OCF$_3$-phenyl | —CH$_2$CH$_2$— | 4-Cl-phenyl |
| A.242 | H | 4-OCF$_3$-phenyl | —CH$_2$CH$_2$— | 4-CH$_3$-phenyl |
| A.243 | H | 4-OCF$_3$-phenyl | —CH$_2$CH$_2$— | 4-OCH$_3$-phenyl |
| A.244 | H | 4-OCF$_3$-phenyl | —CH(CH$_3$)— | 4-Cl-phenyl |
| A.245 | H | 4-OCF$_3$-phenyl | —CH(CH$_3$)— | 4-CH$_3$-phenyl |
| A.246 | H | 4-OCF$_3$-phenyl | —CH(CH$_3$)— | 4-OCH$_3$-phenyl |
| A.247 | CH$_3$ | 4-Cl-phenyl | —CH$_2$CH$_2$— | 4-Cl-phenyl |
| A.248 | CH$_3$ | 4-Cl-phenyl | —CH$_2$CH$_2$— | 4-CH$_3$-phenyl |
| A.249 | CH$_3$ | 4-Cl-phenyl | —CH$_2$CH$_2$— | 4-OCH$_3$-phenyl |
| A.250 | CH$_3$ | 4-Cl-phenyl | —CH(CH$_3$)— | 4-Cl-phenyl |
| A.251 | CH$_3$ | 4-Cl-phenyl | —CH(CH$_3$)— | 4-CH$_3$-phenyl |
| A.252 | CH$_3$ | 4-Cl-phenyl | —CH(CH$_3$)— | 4-OCH$_3$-phenyl |
| A.253 | CH$_3$ | 3,4-di-Cl-phenyl | —CH$_2$CH$_2$— | 4-Cl-phenyl |
| A.254 | CH$_3$ | 3,4-di-Cl-phenyl | —CH$_2$CH$_2$— | 4-CH$_3$-phenyl |
| A.255 | CH$_3$ | 3,4-di-Cl-phenyl | —CH$_2$CH$_2$— | 4-OCH$_3$-phenyl |
| A.256 | CH$_3$ | 3,4-di-Cl-phenyl | —CH(CH$_3$)— | 4-Cl-phenyl |
| A.257 | CH$_3$ | 3,4-di-Cl-phenyl | —CH(CH$_3$)— | 4-CH$_3$-phenyl |
| A.258 | CH$_3$ | 3,4-di-Cl-phenyl | —CH(CH$_3$)— | 4-OCH$_3$-phenyl |
| A.259 | CH$_3$ | 4-Br-phenyl | —CH$_2$CH$_2$— | 4-Cl-phenyl |
| A.260 | CH$_3$ | 4-Br-phenyl | —CH$_2$CH$_2$— | 4-CH$_3$-phenyl |
| A.261 | CH$_3$ | 4-Br-phenyl | —CH$_2$CH$_2$— | 4-OCH$_3$-phenyl |
| A.262 | CH$_3$ | 4-Br-phenyl | —CH(CH$_3$)— | 4-Cl-phenyl |
| A.263 | CH$_3$ | 4-Br-phenyl | —CH(CH$_3$)— | 4-CH$_3$-phenyl |
| A.264 | CH$_3$ | 4-Br-phenyl | —CH(CH$_3$)— | 4-OCH$_3$-phenyl |
| A.265 | H | 3,4-di-OCH$_3$-phenyl | —CH$_2$CH$_2$— | 4-Cl-phenyl |
| A.266 | H | 3,4-di-OCH$_3$-phenyl | —CH$_2$CH$_2$— | 4-CH$_3$-phenyl |
| A.267 | H | 3,4-di-OCH$_3$-phenyl | —CH$_2$CH$_2$— | 4-OCH$_3$-phenyl |
| A.268 | H | 3,4-di-OCH$_3$-phenyl | —CH(CH$_3$)— | 4-Cl-phenyl |
| A.269 | H | 3,4-di-OCH$_3$-phenyl | —CH(CH$_3$)— | 4-CH$_3$-phenyl |
| A.270 | H | 3,4-di-OCH$_3$-phenyl | —CH(CH$_3$)— | 4-OCH$_3$-phenyl |
| A.271 | H | 3,4-di-CH$_3$-phenyl | —CH$_2$CH$_2$— | 4-Cl-phenyl |
| A.272 | H | 3,4-di-CH$_3$-phenyl | —CH$_2$CH$_2$— | 4-CH$_3$-phenyl |
| A.273 | H | 3,4-di-CH$_3$-phenyl | —CH$_2$CH$_2$— | 4-OCH$_3$-phenyl |
| A.274 | H | 3,4-di-CH$_3$-phenyl | —CH(CH$_3$)— | 4-Cl-phenyl |
| A.275 | H | 3,4-di-CH$_3$-phenyl | —CH(CH$_3$)— | 4-CH$_3$-phenyl |
| A.276 | H | 3,4-di-CH$_3$-phenyl | —CH(CH$_3$)— | 4-OCH$_3$-phenyl |
| A.277 | H | 4-Cl-phenyl | —CH$_2$CH$_2$— | 3-OCH$_3$-phenyl |
| A.278 | H | 4-Cl-phenyl | —(CH$_2$)$_3$— | 3,4-di-CH$_3$O-phenyl |

TABLE B (wherein Et means ethyl)

| No. | $R_1$ | n | $R_3$ |
|---|---|---|---|
| B.1 | CH$_3$ | 1 | 4-Cl-phenyl |
| B.2 | Et | 0 | 4-Cl-phenyl |
| B.3 | Et | 1 | 4-Cl-phenyl |
| B.4 | 1-propyl | 0 | 4-Cl-phenyl |
| B.5 | 1-propyl | 1 | 4-Cl-phenyl |
| B.6 | 2-propyl | 0 | 4-Cl-phenyl |
| B.7 | 2-propyl | 1 | 4-Cl-phenyl |
| B.8 | 1-butyl | 0 | 4-Cl-phenyl |
| B.9 | 1-butyl | 1 | 4-Cl-phenyl |
| B.10 | N(CH$_3$)$_2$ | 0 | 4-Cl-phenyl |
| B.11 | N(CH$_3$)$_2$ | 1 | 4-Cl-phenyl |
| B.12 | 1-pyrrolidin | 1 | 4-Cl-phenyl |
| B.13 | 3-Cl-propyl | 1 | 4-Cl-phenyl |
| B.14 | 2-Me-2-propyl | 0 | 4-Cl-phenyl |
| B.15 | 2-Me-propyl | 1 | 4-Cl-phenyl |
| B.16 | CF$_3$ | 1 | 4-Cl-phenyl |
| B.17 | CH$_2$—CF$_3$ | 1 | 4-Cl-phenyl |
| B.18 | vinyl | 1 | 4-Cl-phenyl |
| B.19 | cyclopentyl | 0 | 4-Cl-phenyl |
| B.20 | cyclohexyl | 0 | 4-Cl-phenyl |
| B.21 | cyclopentyl | 1 | 4-Cl-phenyl |
| B.22 | cyclohexyl | 1 | 4-Cl-phenyl |
| B.23 | CH$_2$—SO$_2$—CH$_3$ | 1 | 4-Cl-phenyl |
| B.24 | phenyl | 1 | 4-Cl-phenyl |
| B.25 | benzyl | 1 | 4-Cl-phenyl |
| B.26 | 4-Me-phenyl | 1 | 4-Cl-phenyl |
| B.27 | 4-MeS-phenyl | 1 | 4-Cl-phenyl |
| B.28 | 4-CF$_3$-phenyl | 1 | 4-Cl-phenyl |
| B.29 | 4-CF$_3$O-phenyl | 1 | 4-Cl-phenyl |
| B.30 | 4-MeO-phenyl | 1 | 4-Cl-phenyl |
| B.31 | 3-CH$_3$OOC-phenyl | 1 | 4-Cl-phenyl |
| B.32 | 3-CH$_3$CO-phenyl | 1 | 4-Cl-phenyl |
| B.33 | 4-Cl-phenyl | 1 | 4-Cl-phenyl |
| B.34 | 3-NO$_2$-phenyl | 1 | 4-Cl-phenyl |
| B.35 | 3-CN-phenyl | 1 | 4-Cl-phenyl |
| B.36 | CH$_3$ | 1 | 3,4-di-Cl-phenyl |
| B.37 | Et | 0 | 3,4-di-Cl-phenyl |
| B.38 | Et | 1 | 3,4-di-Cl-phenyl |
| B.39 | 1-propyl | 0 | 3,4-di-Cl-phenyl |
| B.40 | 1-propyl | 1 | 3,4-di-Cl-phenyl |
| B.41 | 2-propyl | 0 | 3,4-di-Cl-phenyl |
| B.42 | 2-propyl | 1 | 3,4-di-Cl-phenyl |
| B.43 | 1-butyl | 0 | 3,4-di-Cl-phenyl |
| B.44 | 1-butyl | 1 | 3,4-di-Cl-phenyl |
| B.45 | N(CH$_3$)$_2$ | 0 | 3,4-di-Cl-phenyl |
| B.46 | N(CH$_3$)$_2$ | 1 | 3,4-di-Cl-phenyl |

TABLE B-continued (wherein Et means ethyl)

| No. | R₁ | n | R₃ |
|---|---|---|---|
| B.47 | 1-pyrrolidin | 1 | 3,4-di-Cl-phenyl |
| B.48 | 3-Cl-propyl | 1 | 3,4-di-Cl-phenyl |
| B.49 | 2-Me-2-propyl | 0 | 3,4-di-Cl-phenyl |
| B.50 | 2-Me-propyl | 1 | 3,4-di-Cl-phenyl |
| B.51 | CF₃ | 1 | 3,4-di-Cl-phenyl |
| B.52 | CH₂—CF₃ | 1 | 3,4-di-Cl-phenyl |
| B.53 | vinyl | 1 | 3,4-di-Cl-phenyl |
| B.54 | cyclopentyl | 0 | 3,4-di-Cl-phenyl |
| B.55 | cyclohexyl | 0 | 3,4-di-Cl-phenyl |
| B.56 | cyclopentyl | 1 | 3,4-di-Cl-phenyl |
| B.57 | cyclohexyl | 1 | 3,4-di-Cl-phenyl |
| B.58 | CH₂—SO₂—CH₃ | 1 | 3,4-di-Ci-phenyl |
| B.59 | phenyl | 1 | 3,4-di-Cl-phenyl |
| B.60 | benzyl | 1 | 3,4-di-Cl-phenyl |
| B.61 | 4-Me-phenyl | 1 | 3,4-di-Cl-phenyl |
| B.62 | 4-MeS-phenyl | 1 | 3,4-di-Cl-phenyl |
| B.63 | 4-CF₃-phenyl | 1 | 3,4-di-Cl-phenyl |
| B.64 | 4-CF₃O-phenyl | 1 | 3,4-di-Cl-phenyl |
| B.65 | 4-MeO-phenyl | 1 | 3,4-di-Cl-phenyl |
| B.66 | 3-CH₃OOC-phenyl | 1 | 3,4-di-Cl-phenyl |
| B.67 | 3-CH₃CO-phenyl | 1 | 3,4-di-Cl-phenyl |
| B.68 | 4-Cl-phenyl | 1 | 3,4-di-Cl-phenyl |
| B.69 | 3-NO₂-phenyl | 1 | 3,4-di-Cl-phenyl |
| B.70 | 3-CN-phenyl | 1 | 3,4-di-Cl-phenyl |
| B.71 | CH₃ | 1 | phenyl |
| B.72 | Et | 0 | phenyl |
| B.73 | Et | 1 | phenyl |
| B.74 | 2-propyl | 0 | phenyl |
| B.75 | 2-propyl | 1 | phenyl |
| B.76 | N(CH₃)₂ | 1 | phenyl |
| B.77 | CH₃ | 1 | 4-Br-phenyl |
| B.78 | Et | 0 | 4-Br-phenyl |
| B.79 | Et | 1 | 4-Br-phenyl |
| B.80 | 2-propyl | 0 | 4-Br-phenyl |
| B.81 | 2-propyl | 1 | 4-Br-phenyl |
| B.82 | N(CH₃)₂ | 1 | 4-Br-phenyl |
| B.83 | CH₃ | 1 | 4-CH₃-phenyl |
| B.84 | Et | 0 | 4-CH₃-phenyl |
| B.85 | Et | 1 | 4-CH₃-phenyl |
| B.86 | 2-propyl | 0 | 4-CH₃-phenyl |
| B.87 | 2-propyl | 1 | 4-CH₃-phenyl |
| B.88 | N(CH₃)₂ | 1 | 4-CH₃-phenyl |
| B.89 | CH₃ | 1 | 4-CH₃O-phenyl |
| B.90 | Et | 0 | 4-CH₃O-phenyl |
| B.91 | Et | 1 | 4-CH₃O-phenyl |
| B.92 | 2-propyl | 0 | 4-CH₃O-phenyl |
| B.93 | 2-propyl | 1 | 4-CH₃O-phenyl |
| B.94 | N(CH₃)₂ | 1 | 4-CH₃O-phenyl |
| B.95 | CH₃ | 1 | 4-CF₃-phenyl |
| B.96 | Et | 0 | 4-CF₃-phenyl |
| B.97 | Et | 1 | 4-CF₃-phenyl |
| B.98 | 2-propyl | 0 | 4-CF₃-phenyl |
| B.99 | 2-propyl | 1 | 4-CF₃-phenyl |
| B.100 | N(CH₃)₂ | 1 | 4-CF₃-phenyl |
| B.101 | CH₃ | 1 | 4-F-phenyl |
| B.102 | Et | 0 | 4-F-phenyl |
| B.103 | Et | 1 | 4-F-phenyl |
| B.104 | 2-propyl | 0 | 4-F-phenyl |
| B.105 | 2-propyl | 1 | 4-F-phenyl |
| B.106 | N(CH₃)₂ | 1 | 4-F-phenyl |
| B.107 | CH₃ | 1 | 4-CF₃O-phenyl |
| B.108 | Et | 0 | 4-CF₃O-phenyl |
| B.109 | Et | 1 | 4-CF₃O-phenyl |
| B.110 | 2-propyl | 0 | 4-CF₃O-phenyl |
| B.111 | 2-propyl | 1 | 4-CF₃O-phenyl |
| B.112 | N(CH₃)₂ | 1 | 4-CF₃O-phenyl |
| B.113 | CH₃ | 1 | 3,4-di-CH₃-phenyl |
| B.114 | Et | 0 | 3,4-di-CH₃-phenyl |
| B.115 | Et | 1 | 3,4-di-CH₃-phenyl |
| B.116 | 2-propyl | 0 | 3,4-di-CH₃-phenyl |
| B.117 | 2-propyl | 1 | 3,4-di-CH₃-phenyl |
| B.118 | N(CH₃)₂ | 1 | 3,4-di-CH₃-phenyl |
| B.119 | CH₃ | 1 | 4-vinyl-phenyl |
| B.120 | Et | 0 | 4-vinyl-phenyl |
| B.121 | Et | 1 | 4-vinyl-phenyl |
| B.122 | 2-propyl | 0 | 4-vinyl-phenyl |
| B.123 | 2-propyl | 1 | 4-vinyl-phenyl |
| B.124 | N(CH₃)₂ | 1 | 4-vinyl-phenyl |
| B.125 | CH₃ | 1 | 4-ethynyl-phenyl |
| B.126 | Et | 0 | 4-ethynyl-phenyl |
| B.127 | Et | 1 | 4-ethynyl-phenyl |
| B.128 | 2-propyl | 0 | 4-ethynyl-phenyl |
| B.129 | 2-propyl | 1 | 4-ethynyl-phenyl |
| B.130 | N(CH₃)₂ | 1 | 4-ethynyl-phenyl |
| B.131 | CH₃ | 1 | 4-cyclopentyl-phenyl |
| B.132 | Et | 0 | 4-cyclopentyl-phenyl |
| B.133 | Et | 1 | 4-cyclopentyl-phenyl |
| B.134 | 2-propyl | 0 | 4-cyclopentyl-phenyl |
| B.135 | 2-propyl | 1 | 4-cyclopentyl-phenyl |
| B.136 | N(CH₃)₂ | 1 | 4-cyclopentyl-phenyl |
| B.137 | Et | 0 | 4-allylO-phenyl |
| B.138 | Et | 1 | 4-allylO-phenyl |
| B.139 | 2-propyl | 0 | 4-allylO-phenyl |
| B.140 | 2-propyl | 1 | 4-allylO-phenyl |
| B.141 | N(CH₃)₂ | 1 | 4-allylO-phenyl |
| B.142 | Et | 0 | 4-CH₃S-phenyl |
| B.143 | Et | 1 | 4-CH₃S-phenyl |
| B.144 | 2-propyl | 0 | 4-CH₃S-phenyl |
| B.145 | 2-propyl | 1 | 4-CH₃S-phenyl |
| B.146 | N(CH₃)₂ | 1 | 4-CH₃S-phenyl |
| B.147 | Et | 0 | 4-CH₃-SO₂-phenyl |
| B.148 | Et | 1 | 4-CH₃-SO₂-phenyl |
| B.149 | 2-propyl | 0 | 4-CH₃-SO₂-phenyl |
| B.150 | 2-propyl | 1 | 4-CH₃-SO₂-phenyl |
| B.151 | N(CH₃)₂ | 1 | 4-CH₃-SO₂-phenyl |
| B.152 | Et | 0 | 3-CH₃CO-phenyl |
| B.153 | Et | 1 | 3-CH₃CO-phenyl |
| B.154 | 2-propyl | 0 | 3-CH₃CO-phenyl |
| B.155 | 2-propyl | 1 | 3-CH₃CO-phenyl |
| B.156 | N(CH₃)₂ | 1 | 3-CH₃CO-phenyl |
| B.157 | Et | 0 | 3-CH₃OOC-phenyl |
| B.158 | Et | 1 | 3-CH₃OOC-phenyl |
| B.159 | 2-propyl | 0 | 3-CH₃OOC-phenyl |
| B.160 | 2-propyl | 1 | 3-CH₃OOC-phenyl |
| B.161 | N(CH₃)₂ | 1 | 3-CH₃OOC-phenyl |
| B.162 | Et | 0 | 4-N(CH₃)₂-phenyl |
| B.163 | Et | 1 | 4-N(CH₃)₂-phenyl |
| B.164 | 2-propyl | 0 | 4-N(CH₃)₂-phenyl |
| B.165 | 2-propyl | 1 | 4-N(CH₃)₂-phenyl |
| B.166 | N(CH₃)₂ | 1 | 4-N(CH₃)₂-phenyl |
| B.167 | Et | 0 | 3-NO₂-phenyl |
| B.168 | Et | 1 | 3-NO₂-phenyl |
| B.169 | 2-propyl | 0 | 3-NO₂-phenyl |
| B.170 | 2-propyl | 1 | 3-NO₂-phenyl |
| B.171 | N(CH₃)₂ | 1 | 3-NO₂-phenyl |
| B.172 | Et | 0 | 4-CN-phenyl |
| B.173 | Et | 1 | 4-CN-phenyl |
| B.174 | 2-propyl | 0 | 4-CN-phenyl |
| B.175 | 2-propyl | 1 | 4-CN-phenyl |
| B.176 | N(CH₃)₂ | 1 | 4-CN-phenyl |
| B.177 | Et | 0 | 4-OH-phenyl |
| B.178 | Et | 1 | 4-OH-phenyl |
| B.179 | 2-propyl | 0 | 4-OH-phenyl |
| B.180 | 2-propyl | 1 | 4-OH-phenyl |
| B.181 | N(CH₃)₂ | 1 | 4-OH-phenyl |
| B.182 | Et | 0 | 2-thienyl |
| B.183 | Et | 1 | 2-thienyl |
| B.184 | 2-propyl | 0 | 2-thienyl |
| B.185 | 2-propyl | 1 | 2-thienyl |
| B.186 | N(CH₃)₂ | 1 | 2-thienyl |
| B.187 | Et | 0 | 3-thienyl |
| B.188 | Et | 1 | 3-thienyl |
| B.189 | 2-propyl | 0 | 3-thienyl |
| B.190 | 2-propyl | 1 | 3-thienyl |
| B.191 | N(CH₃)₂ | 1 | 3-thienyl |
| B.192 | Et | 0 | 2-furanyl |
| B.193 | Et | 1 | 2-furanyl |
| B.194 | 2-propyl | 0 | 2-furanyl |
| B.195 | 2-propyl | 1 | 2-furanyl |
| B.196 | N(CH₃)₂ | 1 | 2-furanyl |

TABLE B-continued (wherein Et means ethyl)

| No. | $R_1$ | n | $R_3$ |
|---|---|---|---|
| B.197 | Et | 0 | 1-naphthyl |
| B.198 | Et | 1 | 1-naphthyl |
| B.199 | 2-propyl | 0 | 1-naphthyl |
| B.200 | 2-propyl | 1 | 1-naphthyl |
| B.201 | $N(CH_3)_2$ | 1 | 1-naphthyl |
| B.202 | Et | 0 | 2-naphthyl |
| B.203 | Et | 1 | 2-naphthyl |
| B.204 | 2-propyl | 0 | 2-naphthyl |
| B.205 | 2-propyl | 1 | 2-naphthyl |
| B.206 | $N(CH_3)_2$ | 1 | 2-naphthyl |
| B.207 | Et | 0 | 3-pyridyl |
| B.208 | Et | 1 | 3-pyridyl |
| B.209 | 2-propyl | 0 | 3-pyridyl |
| B.210 | 2-propyl | 1 | 3-pyridyl |
| B.211 | $N(CH_3)_2$ | 1 | 3-pyridyl |
| B.212 | Et | 0 | 2-benzothiazolyl |
| B.213 | Et | 1 | 2-benzothiazolyl |
| B.214 | 2-propyl | 0 | 2-benzothiazolyl |
| B.215 | 2-propyl | 1 | 2-benzothiazolyl |
| B.216 | $N(CH_3)_2$ | 1 | 2-benzothiazolyl |
| B.217 | Et | 0 | 3-indolyl |
| B.218 | Et | 1 | 3-indolyl |
| B.219 | 2-propyl | 0 | 3-indolyl |
| B.220 | 2-propyl | 1 | 3-indolyl |
| B.221 | $N(CH_3)_2$ | 1 | 3-indolyl |
| B.222 | Et | 0 | 3-$CF_3$-phenyl |
| B.223 | Et | 1 | 3-$CF_3$-phenyl |
| B.224 | 2-propyl | 0 | 3-$CF_3$-phenyl |
| B.225 | 2-propyl | 1 | 3-$CF_3$-phenyl |
| B.226 | $N(CH_3)_2$ | 1 | 3-$CF_3$-phenyl |
| B.227 | Et | 0 | 4-phenoxy-phenyl |
| B.228 | Et | 1 | 4-phenoxy-phenyl |
| B.229 | 2-propyl | 0 | 4-phenoxy-phenyl |
| B.230 | 2-propyl | 1 | 4-phenoxy-phenyl |
| B.231 | $N(CH_3)_2$ | 1 | 4-phenoxy-phenyl |
| B.232 | Et | 0 | 4-ethoxy-phenyl |
| B.233 | Et | 1 | 4-ethoxy-phenyl |
| B.234 | 2-propyl | 0 | 4-ethoxy-phenyl |
| B.235 | 2-propyl | 1 | 4-ethoxy-phenyl |
| B.236 | $N(CH_3)_2$ | 1 | 4-ethoxy-phenyl |
| B.237 | Et | 0 | 3,4-O—$CH_2$—O-phenyl |
| B.238 | Et | 1 | 3,4-O—$CH_2$—O-phenyl |
| B.239 | 2-propyl | 0 | 3,4-O—$CH_2$—O-phenyl |
| B.240 | 2-propyl | 1 | 3,4-O—$CH_2$—O-phenyl |
| B.241 | $N(CH_3)_2$ | 1 | 3,4-O—$CH_2$—O-phenyl |
| B.242 | Et | 0 | 3,4-O—$CH_2CH_2$—O-phenyl |
| B.243 | Et | 1 | 3,4-O—$CH_2CH_2$—O-phenyl |
| B.244 | 2-propyl | 0 | 3,4-O—$CH_2CH_2$—O-phenyl |
| B.245 | 2-propyl | 1 | 3,4-O—$CH_2CH_2$—O-phenyl |
| B.246 | $N(CH_3)_2$ | 1 | 3,4-O—$CH_2CH_2$—O-phenyl |
| B.247 | Et | 0 | 4-biphenyl |
| B.248 | Et | 1 | 4-biphenyl |
| B.249 | 2-propyl | 0 | 4-biphenyl |
| B.250 | 2-propyl | 1 | 4-biphenyl |
| B.251 | $N(CH_3)_2$ | 1 | 4-biphenyl |
| B.252 | Et | 0 | 4-isopropyl-phenyl |
| B.253 | Et | 1 | 4-isopropyl-phenyl |
| B.254 | 2-propyl | 0 | 4-isopropyl-phenyl |
| B.255 | 2-propyl | 1 | 4-isopropyl-phenyl |
| B.256 | $N(CH_3)_2$ | 1 | 4-isopropyl-phenyl |
| B.257 | Et | 0 | 4-$CH_3$OOC-phenyl |
| B.258 | Et | 1 | 4-$CH_3$OOC-phenyl |
| B.259 | 2-propyl | 0 | 4-$CH_3$OOC-phenyl |
| B.260 | 2-propyl | 1 | 4-$CH_3$OOC-phenyl |
| B.261 | $N(CH_3)_2$ | 1 | 4-$CH_3$OOC-phenyl |
| B.262 | Et | 0 | 3,4-di-F-phenyl |
| B.263 | Et | 1 | 3,4-di-F-phenyl |
| B.264 | 2-propyl | 0 | 3,4-di-F-phenyl |
| B.265 | 2-propyl | 1 | 3,4-di-F-phenyl |
| B.266 | $N(CH_3)_2$ | 1 | 3,4-di-F-phenyl |
| B.267 | Et | 0 | 4-tert.butyl-phenyl |
| B.268 | Et | 1 | 4-tert.butyl-phenyl |
| B.269 | 2-propyl | 0 | 4-tert.butyl-phenyl |
| B.270 | 2-propyl | 1 | 4-tert.butyl-phenyl |
| B.271 | $N(CH_3)_2$ | 1 | 4-tert.butyl-phenyl |
| B.272 | Et | 0 | 3-Cl-phenyl |
| B.273 | Et | 1 | 3-Cl-phenyl |
| B.274 | 2-propyl | 0 | 3-Cl-phenyl |
| B.275 | 2-propyl | 1 | 3-Cl-phenyl |
| B.276 | $N(CH_3)_2$ | 1 | 3-Cl-phenyl |
| B.277 | Et | 0 | 3,5-di-Cl-phenyl |
| B.278 | Et | 1 | 3,5-di-Cl-phenyl |
| B.279 | 2-propyl | 0 | 3,5-di-Cl-phenyl |
| B.280 | 2-propyl | 1 | 3,5-di-Cl-phenyl |
| B.281 | $N(CH_3)_2$ | 1 | 3,5-di-Cl-phenyl |
| B.282 | Et | 0 | 3-pyrazolyl |
| B.283 | Et | 1 | 3-pyrazolyl |
| B.284 | 2-propyl | 0 | 3-pyrazolyl |
| B.285 | 2-propyl | 1 | 3-pyrazolyl |
| B.286 | $N(CH_3)_2$ | 1 | 3-pyrazolyl |
| B.287 | Et | 0 | 1-Me-2-benzimidazolyl |
| B.288 | Et | 1 | 1-Me-2-benzimidazoiyl |
| B.289 | 2-propyl | 0 | 1-Me-2-benzimidazolyl |
| B.290 | 2-propyl | 1 | 1-Me-2-benzimidazolyl |
| B.291 | $N(CH_3)_2$ | 1 | 1-Me-2-benzimidazolyl |
| B.292 | Et | 0 | 2-thiazolyl |
| B.293 | Et | 1 | 2-thiazolyl |
| B.294 | 2-propyl | 0 | 2-thiazolyl |
| B.295 | 2-propyl | 1 | 2-thiazolyl |
| B.296 | $N(CH_3)_2$ | 1 | 2-thiazolyl |
| B.297 | Et | 0 | 1-Me-3-indolyl |
| B.298 | Et | 1 | 1-Me-3-indolyl |
| B.299 | 2-propyl | 0 | 1-Me-3-indolyl |
| B.300 | 2-propyl | 1 | 1-Me-3-indolyl |
| B.301 | $N(CH_3)_2$ | 1 | 1-Me-3-indolyl |
| B.302 | Et | 0 | 2-pyrrolyl |
| B.303 | Et | 1 | 2-pyrrolyl |
| B.304 | 2-propyl | 0 | 2-pyrrolyl |
| B.305 | 2-propyl | 1 | 2-pyrrolyl |
| B.306 | $N(CH_3)_2$ | 1 | 2-pyrrolyl |
| B.307 | Et | 0 | 2-imidazolyl |
| B.308 | Et | 1 | 2-imidazolyl |
| B.309 | 2-propyl | 0 | 2-imidazolyl |
| B.310 | 2-propyl | 1 | 2-imidazolyl |
| B.311 | $N(CH_3)_2$ | 1 | 2-imidazolyl |
| B.312 | Et | 0 | 4-imidazolyl |
| B.313 | Et | 1 | 4-imidazolyl |
| B.314 | 2-propyl | 0 | 4-imidazolyl |
| B.315 | 2-propyl | 1 | 4-imidazolyl |
| B.316 | $N(CH_3)_2$ | 1 | 4-imidazolyl |
| B.317 | 1-propyl | 1 | 4-$CF_3$O-phenyl |
| B.318 | Et | 1 | 3,4-di-$CH_3$O-phenyl |
| B.319 | 1-propyl | 1 | 4-Br-phenyl |
| B.320 | $N(CH_3)_2$ | 1 | 3,4-di-$CH_3$O-phenyl |
| B.321 | 1-propyl | 1 | 3,4-di-$CH_3$O-phenyl |
| B.322 | 1-propyl | 1 | 4-$N(CH_3)_2$-phenyl |
| B.323 | 1-propyl | 1 | 4-$CH_3$S-phenyl |
| B.324 | Et | 1 | 3-$CH_3$-phenyl |
| B.325 | $N(CH_3)_2$ | 1 | 3-$CH_3$-phenyl |
| B.326 | 1-propyl | 1 | 3-$CH_3$-phenyl |
| B.327 | 1-propyl | 1 | 4-$CH_3$-phenyl |
| B.328 | $N(CH_3)_2$ | 1 | 3-$CF_3$-phenyl |
| B.329 | 1-propyl | 1 | 3-$CF_3$-phenyl |
| B.330 | 1-propyl | 1 | 4-phenoxy-phenyl |
| B.331 | 1-propyl | 1 | 4-ethoxy-phenyl |
| B.332 | 1-propyl | 1 | 3,4-O-$CH_2$-O-phenyl |
| B.333 | $CH_3$ | 1 | 3-F,4-Cl-phenyl |
| B.334 | Et | 1 | 3-F,4-Cl-phenyl |
| B.335 | $N(CH_3)_2$ | 1 | 3-F,4-Cl-phenyl |
| B.336 | $N(CH_3)_2$ | 1 | 3-$CF_3$,4-Cl-phenyl |
| B.337 | Et | 1 | 3-$CF_3$,4-Cl-phenyl |
| B.338 | $CH_3$ | 1 | 3-$CF_3$,4-Cl-phenyl |
| B.339 | Et | 1 | 3-F-phenyl |
| B.340 | Et | 1 | 5-Me,2-thienyl |
| B.341 | 1-propyl | 1 | 2-naphthyl |
| B.342 | n-butyl | 1 | 4-Br-phenyl |
| B.343 | vinyl | 1 | 4-Br-phenyl |
| B.344 | 4-Me-phenyl | 1 | 4-Br-phenyl |
| B.345 | Et | 1 | 2-$CH_3$O-phenyl |
| B.346 | Et | 1 | 3-$CH_3$O-phenyl |

TABLE B-continued (wherein Et means ethyl)

| No. | R₁ | n | R₃ |
|---|---|---|---|
| B.347 | Et | 1 | 2-Cl-phenyl |
| B.348 | Et | 1 | 3,5-di-F-phenyl |
| B.349 | Et | 1 | 3-CH₃,4-CH₃O-phenyl |
| B.350 | Et | 1 | 4-NHCOCH₃-phenyl |
| B.351 | Et | 1 | 3,5-di-CH₃O-phenyl |
| B.352 | Et | 1 | 4-pyrrolidino-phenyl |
| B.353 | Et | 1 | 3-Br-phenyl |
| B.354 | Et | 1 | 3-CH₃O,4-propargyloxy-phenyl |
| B.355 | Et | 1 | 4-Br,2-thienyl |
| B.356 | Et | 1 | 2-fluorenyl |
| B.357 | Et | 1 | 4-CH(O-Et)₂-phenyl |
| B.358 | Et | 1 | 4-(4'-Cl-phenoxy)-phenyl |
| B.359 | Et | 1 | 5-Me,2-furanyl |
| B.360 | Et | 1 | 3-Cl-phenyl |
| B.361 | Et | 1 | 4-NO₂-phenyl |
| B.362 | Et | 1 | 2,4-di-CH₃O-phenyl |
| B.363 | Et | 1 | 2,4-di-Cl-phenyl |
| B.364 | N(CH₃)₂ | 1 | 5-Me,2-furanyl |
| B.365 | N(CH₃)₂ | 1 | 3-F-phenyl |
| B.366 | N(CH₃)₂ | 1 | 5-Me,2-thienyl |
| B.367 | N(CH₃)₂ | 1 | 2-CH₃O-phenyl |
| B.368 | N(CH₃)₂ | 1 | 3-CH₃O-phenyl |
| B.369 | N(CH₃)₂ | 1 | 2-Cl-phenyl |
| B.370 | N(CH₃)₂ | 1 | 3,5-di-F-phenyl |
| B.371 | N(CH₃)₂ | 1 | 3-CH₃,4-CH₃O-phenyl |
| B.372 | N(CH₃)₂ | 1 | 4-NO₂-phenyl |
| B.373 | N(CH₃)₂ | 1 | 3,5-di-CH₃O-phenyl |
| B.374 | N(CH₃)₂ | 1 | 2,4-di-CH₃O-phenyl |
| B.375 | N(CH₃)₂ | 1 | 2,4-di-Cl-phenyl |
| B.376 | N(CH₃)₂ | 1 | 4-pyrrolidino-phenyl |
| B.377 | N(CH₃)₂ | 1 | 3-Br-phenyl |
| B.378 | N(CH₃)₂ | 1 | 3-CH₃O,4-propargyloxy-phenyl |
| B.379 | N(CH₃)₂ | 1 | 4-Br,2-thienyl |
| B.380 | N(CH₃)₂ | 1 | 4-(4'-Cl-phenoxy)-phenyl |
| B.381 | N(CH₃)₂ | 1 | 2-fluorenyl |

Preparation Examples for the Compounds of Formula I

EXAMPLE 1

2-(4-Chloro-phenyl)-N-[2-(3,4-dimethoxy-phenyl)-ethyl]-2-ethanesulfonylamino-acetamide

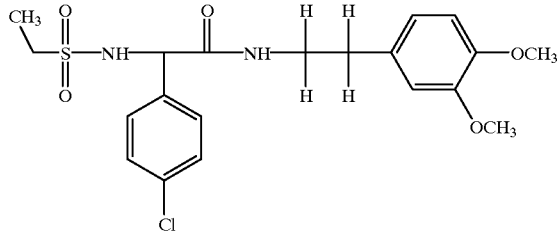

To a vigorously stirred solution of 8 g amino-(4-chloro-phenyl)-acetic acid (J.Chem.Soc.,1962,1440) and 1.7 g sodium hydroxide in 125 ml water at 0° C. is added simultaneously a solution of 5.6 g ethanesulfonyl chloride in 100 ml toluene and a solution of 1.7 g sodium hydroxide in 100 ml water during 20 minutes. The reaction mixture is stirred for 45 min at 0° C. Stirring is continued for 3 hours during which the reaction mixture is allowed to warm to room temperature.

The organic phase is separated and extracted with 100 ml 2N sodium hydroxide solution. The water phases are combined and acidified with conc. hydrochloric acid to pH<2 and extracted with ethyl acetate (2×500 ml). The organic phases are washed with brine solution (2×150 ml), dried over magnesium sulfate and evaporated to dryness, yielding (4-chloro-phenyl)-ethanesulfonamino-acetic acid as yellow oil.

To a solution of 2.5 g (4-chloro-phenyl)-ethanesulfonamino-acetic acid, 1.6 g homoveratrylamine and 3.1 ml N,N-diisopropylethylamine in 40 ml N,N-dimethylformamide is added 4 g benzotriazol-1-yloxy-tris (dimethylamino)phosphonium hexafluorophosphate. The reaction mixture is stirred for 2 hours at room temperature. 500 ml water is added and extracted twice with ethyl acetate (2×300 ml). The organic phases are washed with brine (2×100 ml), combined, died over magnesium sulfate and evaporated to dryness. The residue is purified by flash column chromatography on silica get using ethyl acetate/hexane 2:1 as eluent. 2-(4-chloro-phenyl)-N-[2-(3,4-dimethoxy-phenyl)-ethyl]-2-ethanesulfonylamino-acetamide is obtained (cmpd. Tab.14,B.3) and recrystallized from ethyl acetate/hexane, m.p. 136–138° C.

EXAMPLE 2

2-Benzo[1,3]dioxol-5-yl-N-[2-(3,4-dimethoxy-phenyl)-ethyl]-2-(N',N'-dimethylsulfamido)-acetamide

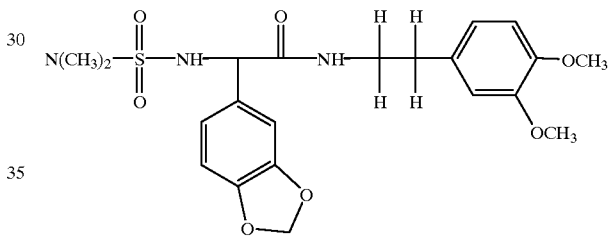

A mixture of 4.78 g (25.0 mmol) 4-(2-isocyano-ethyl)-1,2-dimethoxy-benzene, 4.5 g (30 mmol) piperonal, 3.15 g (50 mmol) ammonium formiate in 25 ml methanol (which has been previously purged by a nitrogen stream) is heated at reflux for 18 hours. The solution is cooled to 0° C. and 10 ml HCl 10M in methanol is added. The reaction mixture is stirred at RT for 10 hours. The mixture is then extracted with 2 fold 150 ml ice-cooled water. The water phase is made basic by the addition of NaOH 2N (pH=14) and is extracted with ethyl acetate. 7.33 g (82%) 2-amino-2-benzo[1,3]dioxol-5-yl-N-[2-(3,4-dimethoxy-phenyl)-ethyl]acetamide is isolated as an orange oil which is further reacted without purification. 1.9 g (5.3 mmol) 2-amino-2-benzo[1,3]dioxol-5-yl-N-[2-(3,4-dimethoxy-phenyl)-ethyl]-acetamide is dissolved in 20 ml THF and cooled to 0° C. 0.8 ml (7.42 mmol) N,N-dimethyl-sulfamoyl chloride and 2.22 ml (15.9 mmol) triethylamine are added and the mixture is stirred 15 hours at RT. After dilution with ethyl acetate, the mixture is extracted with ice-cooled water. Evaporation of the solvent give an oil which is crystallized in toluene to give 1.08 g (44%) 2-benzo[1,3]dioxol-5-yl-N-[2-(3,4-dimethoxy-phenyl)-ethyl]-2-(N',N'-dimethylsulfamido)-acetamide (cmpd. Tab.14,B.241) as a white solid (m.p. 137.5–139° C.). From the mother liquor 0.85 g (35%) compound is further isolated.

The compounds given in Table C can be obtained analogously to Examples 1 or 2.

TABLE C

| Compound | Stereochemistry | physical data m.p. or M(ESMS) |
|---|---|---|
| Tab.2, A.277 | R, S | 113–115 |
| Tab.2, A.278 | R, S | 123–124° C. |
| Tab.14, B.3 | R, S | 136–138° C. |
| Tab.14, B.38 | R, S | 473(M − 1)− |
| Tab.14, B.38 | R | 126–127° C. |
| Tab.14, B.46 | R | oil |
| Tab.14, B.73 | R, S | 157–159° C. |
| Tab.14, B.77 | R, S | 167–168.5° C. |
| Tab.14, B.79 | R, S | 143–145° C. |
| Tab.14, B.81 | R, S | 497(M − 1)− |
| Tab.14, B.82 | R, S | 114–116° C. |
| Tab.14, B.85 | R, S | 135–136° C. |
| Tab.14, B.88 | R, S | 118.5–119.5° C. |
| Tab.14, B.91 | R, S | 116–127° C.; 437(M + 1)+ |
| Tab.14, B.94 | R, S | 452(M + 1)+ |
| Tab.14, B.97 | R, S | 150–153° C. |
| Tab.14, B.103 | R, S | 161–163° C. |
| Tab.14, B.109 | R, S | 154–155° C. |
| Tab.14, B.112 | R, S | 506(M + 1)+ |
| Tab.14, B.143 | R, S | 155.5–156.5° C. |
| Tab.14, B.146 | R, S | 102.5–104.5° C. |
| Tab.14, B.163 | R, S | 146–148° C. |
| Tab.14, B.166 | R, S | 109–110° C. |
| Tab.14, B.173 | R, S | 145–147° C. |
| Tab.14, B.176 | R, S | 445(M − 1)− |
| Tab.14, B.183 | R, S | 136–137.5° C. |
| Tab.14, B.186 | R, S | 426(M − 1)− |
| Tab.14, B.193 | R, S | 395(M − 1)− |
| Tab.14, B.196 | R, S | 410(M − 1)− |
| Tab.14, B.198 | R, S | 144–146° C. |
| Tab.14, B.201 | R, S | 470(M − 1)− |
| Tab.14, B.203 | R, S | 135–136.5° C. |
| Tab.14, B.206 | R, S | 472(M + 1)+ |
| Tab.14, B.223 | R, S | 103–107° C. |
| Tab.14, B.228 | R, S | 134–136° C. |
| Tab.14, B.231 | R, S | 128.5–131° C. |
| Tab.14, B.233 | R, S | 137.5–138.5° C. |
| Tab.14, B.236 | R, S | 119–121 |
| Tab.14, B.238 | R, S | 188–189.5° C. |
| Tab.14, B.241 | R, S | 137.5–139° C. |
| Tab.14, B.248 | R, S | 144–144.5° C.; 483(M + 1)+ |
| Tab.14, B.251 | R, S | 125–126.5° C.; 498(M + 1)+ |
| Tab.14, B.253 | R, S | 163–164° C. |
| Tab.14, B.256 | R, S | 464(M + 1)+ |
| Tab.14, B.258 | R, S | 140–141.5° C.; 465(M + 1)+ |
| Tab.14, B.261 | R, S | 126–127° C.; 480(M + 1)+ |
| Tab.14, B.263 | R, S | 149.5–151° C. |
| Tab.14, B.266 | R, S | 458(M + 1)+ |
| Tab.14, B.268 | R, S | 174–176° C. |
| Tab.14, B.271 | R, S | 476(M − 1)− |
| Tab.14, B.273 | R, S | 123–125° C. |
| Tab.14, B.276 | R, S | 117–118° C.; 456(M + 1)+ |
| Tab.14, B.278 | R, S | 120.5–122° C. |
| Tab.14, B.281 | R, S | 155–157° C. |
| Tab.14, B.317 | R, S | 115.5–118.5° C. |
| Tab.14, B.318 | R, S | 159.5–160.5° C. |
| Tab.14, B.319 | R, S | 136–137° C. |
| Tab.14, B.320 | R, S | 142–143° C. |
| Tab.14, B.321 | R, S | 139–141° C. |
| Tab.14, B.322 | R, S | 125.5–126.5° C. |
| Tab.14, B.323 | R, S | 130.5–135.5° C. |
| Tab.14, B.324 | R, S | 112.5–113.5° C. |
| Tab.14, B.325 | R, S | 434(M − 1)− |
| Tab.14, B.326 | R, S | 433(M − 1)− |
| Tab.14, B.327 | R, S | 116–117° C. |
| Tab.14, B.328 | R, S | 488(M − 1)− |
| Tab.14, B.329 | R, S | 487(M − 1)− |
| Tab.14, B.330 | R, S | 83–85° C. |
| Tab.14, B.331 | R, S | 132.5–134° C. |
| Tab.14, B.332 | R, S | 134–136° C. |
| Tab.14, B.333 | R, S | 141–142° C. |
| Tab.14, B.334 | R, S | 139–141° C. |
| Tab.14, B.335 | R, S | 122–123° C. |
| Tab.14, B.336 | R, S | oil |
| Tab.14, B.337 | R, S | 115–117° C. |
| Tab.14, B.338 | R, S | 108–110° C. |
| Tab.14, B.339 | R, S | 425(M + 1)+ |
| Tab.14, B.340 | R, S | 427(M + 1)+ |
| Tab.14, B.341 | R, S | 471(M + 1)+ |
| Tab.14, B.342 | R, S | 127.5–129.5° C. |
| Tab.14, B.343 | R, S | 152.5–154.5° C. |
| Tab.14, B.344 | R, S | 166–167° C. |
| Tab.14, B.345 | R, S | 437(M + 1)+ |
| Tab.14, B.346 | R, S | 437(M + 1)+ |
| Tab.14, B.347 | R, S | 441(M + 1)+ |
| Tab.14, B.348 | R, S | 443(M + 1)+ |
| Tab.14, B.349 | R, S | 451(M + 1)+ |
| Tab.14, B.351 | R, S | 467(M + 1)+ |
| Tab.14, B.352 | R, S | 476(M + 1)+ |
| Tab.14, B.353 | R, S | 486(M + 1)+ |
| Tab.14, B.354 | R, S | 491(M + 1)+ |
| Tab.14, B.355 | R, S | 492(M + 1)+ |
| Tab.14, B.359 | R, S | 411(M + 1)+ |
| Tab.14, B.360 | R, S | 441(M + 1)+ |
| Tab.14, B.361 | R, S | 452(M + 1)+ |
| Tab.14, B.362 | R, S | 467(M + 1)+ |
| Tab.14, B.363 | R, S | 476(M + 1)+ |
| Tab.14, B.364 | R, S | 426(M + 1)+ |
| Tab.14, B.365 | R, S | 440(M + 1)+ |
| Tab.14, B.366 | R, S | 442(M + 1)+ |
| Tab.14, B.367 | R, S | 452(M + 1)+ |
| Tab.14, B.368 | R, S | 452(M + 1)+ |
| Tab.14, B.369 | R, S | 456(M + 1)+ |
| Tab.14, B.370 | R, S | 459(M + 1)+ |
| Tab.14, B.371 | R, S | 466(M + 1)+ |
| Tab.14, B.372 | R, S | 467(M + 1)+ |
| Tab.14, B.373 | R, S | 482(M + 1)+ |
| Tab.14, B.374 | R, S | 482(M + 1)+ |
| Tab.14, B.375 | R, S | 491(M + 1)+ |
| Tab.14, B.378 | R, S | 506(M + 1)+ |
| Tab.14, B.379 | R, S | 507(M + 1)+ |
| Tab.14, B.380 | R, S | 549(M + 1)+ |
| Tab.15, B.3 | R, S | 147–148° C. |
| Tab.15, B.73 | R, S | 121–122° C. |
| Tab.15, B.85 | R, S | 147–150° C. |
| Tab.15, B.91 | R, S | 156–158° C. |
| Tab.15, B.97 | R, S | 160–165° C. |
| Tab.15, B.103 | R, S | 141–143° C. |
| Tab.16, B.3 | R, S | 140–145° C. |
| Tab.16, B.91 | R, S | 463(M + 1)+ |
| Tab.16, B.193 | R, S | 437(M + 1)+ |
| Tab.16, B.248 | R, S | 509(M + 1)+ |
| Tab.16, B.258 | R, S | 491(M + 1)+ |
| Tab.16, B.273 | R, S | 467(M + 1)+ |
| Tab.16, B.278 | R, S | 502(M + 1)+ |
| Tab.16, B.334 | R, S | 158–159° C. |
| Tab.16, B.339 | R, S | 451(M + 1)+ |
| Tab.16, B.340 | R, S | 453(M + 1)+ |
| Tab.16, B.345 | R, S | 463(M + 1)+ |
| Tab.16, B.346 | R, S | 463(M + 1)+ |
| Tab.16, B.347 | R, S | 467(M + 1)+ |
| Tab.16, B.348 | R, S | 469(M + 1)+ |
| Tab.16, B.349 | R, S | 478(M + 1)+ |
| Tab.16, B.350 | R, S | 490(M + 1)+ |
| Tab.16, B.351 | R, S | 493(M + 1)+ |
| Tab.16, B.352 | R, S | 502(M + 1)+ |
| Tab.16, B.353 | R, S | 512(M + 1)+ |
| Tab.16, B.354 | R, S | 517(M + 1)+ |
| Tab.16, B.355 | R, S | 518(M + 1)+ |
| Tab.16, B.356 | R, S | 521(M + 1)+ |
| Tab.16, B.357 | R, S | 535(M + 1)+ |
| Tab.16, B.358 | R, S | 560(M + 1)+ |
| Tab.16, B.362 | R, S | 493(M + 1)+ |
| Tab.17, B.1 | R | oil |
| Tab.17, B.3 | R, S | 123–128° C. |
| Tab.17, B.3 | R | 126–127 |
| Tab.17, B.3 | S | oil |
| Tab.17, B.11 | R | oil |

TABLE C-continued

| Compound | Stereochemistry | physical data m.p. or M(ESMS) |
|---|---|---|
| Tab.17, B.79 | R, S | 144–145° C. |
| Tab.17, B.82 | R, S | 115.5–117.5° C. |
| Tab.17, B.85 | R, S | 139.5–140.5° C. |
| Tab.17, B.88 | R, S | 96–97.5° C. |
| Tab.17, B.91 | R, S | 461(M + 1)+ |
| Tab.17, B.94 | R, S | 476(M + 1)+ |
| Tab.17, B.248 | R, S | 507(M + 1)+ |
| Tab.17, B.251 | R, S | 520(M − 1)−; 522(M + 1)+ |
| Tab.17, B.258 | R, S | 489(M + 1)+ |
| Tab.17, B.261 | R, S | 504(M + 1)+ |
| Tab.17, B.273 | R, S | 480(M + 1)+ |
| Tab.17, B.334 | R, S | 135–137° C. |
| Tab.17, B.339 | R, S | 449(M + 1)+ |
| Tab.17, B.340 | R, S | 451(M + 1)+ |
| Tab.17, B.345 | R, S | 461(M + 1)+ |
| Tab.17, B.346 | R, S | 461(M + 1)+ |
| Tab.17, B.347 | R, S | 465(M + 1)+ |
| Tab.17, B.348 | R, S | 467(M + 1)+ |
| Tab.17, B.349 | R, S | 475(M + 1)+ |
| Tab.17, B.350 | R, S | 488(M + 1)+ |
| Tab.17, B.351 | R, S | 491(M + 1)+ |
| Tab.17, B.352 | R, S | 500(M + 1)+ |
| Tab.17, B.353 | R, S | 510(M + 1)+ |
| Tab.17, B.354 | R, S | 515(M + 1)+ |
| Tab.17, B.355 | R, S | 516(M + 1)+ |
| Tab.17, B.356 | R, S | 519(M + 1)+ |
| Tab.17, B.358 | R, S | 558(M + 1)+ |
| Tab.17, B.359 | R, S | 435(M + 1)+ |
| Tab.17, B.360 | R, S | 465(M + 1)+ |
| Tab.17, B.361 | R, S | 476(M + 1)+ |
| Tab.17, B.362 | R, S | 491(M + 1)+ |
| Tab.17, B.363 | R, S | 500(M + 1)+ |
| Tab.17, B.364 | R, S | 450(M + 1)+ |
| Tab.17, B.365 | R, S | 464(M + 1)+ |
| Tab.17, B.366 | R, S | 466(M + 1)+ |
| Tab.17, B.367 | R, S | 476(M + 1)+ |
| Tab.17, B.368 | R, S | 476(M + 1)+ |
| Tab.17, B.369 | R, S | 480(M + 1)+ |
| Tab.17, B.370 | R, S | 482(M + 1)+ |
| Tab.17, B.371 | R, S | 490(M + 1)+ |
| Tab.17, B.372 | R, S | 491(M + 1)+ |
| Tab.17, B.373 | R, S | 506(M + 1)+ |
| Tab.17, B.374 | R, S | 506(M + 1)+ |
| Tab.17, B.375 | R, S | 515(M + 1)+ |
| Tab.17, B.376 | R, S | 515(M + 1)+ |
| Tab.17, B.377 | R, S | 525(M + 1)+ |
| Tab.17, B.378 | R, S | 530(M + 1)+ |
| Tab.17, B.379 | R, S | 531(M + 1)+ |
| Tab.17, B.380 | R, S | 573(M + 1)+ |
| Tab.18, B.3 | diastereomere A (rac.) | 477(M − 1)− |
| Tab.18, B.3 | diastereomere B (rac.) | 477(M − 1)− |
| Tab.18, B.38 | R, S | 130–132° C. |
| Tab.18, B.85 | R, S | 141.5–143.5° C. / 459(M + 1)+ |
| Tab.18, B.88 | R, S | 110.5–113.5° C. / 474(M + 1)+ |
| Tab.18, B.319 | R, S | 161–163° C. |
| Tab.20, B.3 | R, S | 140–143° C. |
| Tab.21, B.3 | R, S | 121–123° C. |
| Tab.21, B.88 | R, S | 119.5–121.5° C. |
| Tab.21, B.91 | R, S | 489(M + 1)+ |
| Tab.21, B.94 | R, S | 504(M + 1)+ |
| Tab.21, B.258 | R, S | 517(M + 1)+ |
| Tab.21, B.261 | R, S | 532(M + 1)+ |
| Tab.21, B.319 | R, S | 110–112° C. |
| Tab.21, B.334 | R, S | 127–128° C. |
| Tab.21, B.339 | R, S | 477(M + 1)+ |
| Tab.21, B.340 | R, S | 479(M + 1)+ |
| Tab.21, B.345 | R, S | 489(M + 1)+ |
| Tab.21, B.347 | R, S | 494(M + 1)+ |
| Tab.21, B.348 | R, S | 495(M + 1)+ |
| Tab.21, B.349 | R, S | 503(M + 1)+ |
| Tab.21, B.351 | R, S | 519(M + 1)+ |
| Tab.21, B.352 | R, S | 528(M + 1)+ |
| Tab.21, B.353 | R, S | 538(M + 1)+ |
| Tab.21, B.354 | R, S | 543(M + 1)+ |
| Tab.21, B.355 | R, S | 544(M + 1)+ |
| Tab.21, B.356 | R, S | 547(M + 1)+ |
| Tab.21, B.358 | R, S | 586(M + 1)+ |
| Tab.21, B.359 | R, S | 463(M + 1)+ |
| Tab.21, B.361 | R, S | 504(M + 1)+ |
| Tab.21, B.362 | R, S | 519(M + 1)+ |
| Tab.21, B.363 | R, S | 528(M + 1)+ |
| Tab.21, B.364 | R, S | 478(M + 1)+ |
| Tab.21, B.365 | R, S | 492(M + 1)+ |
| Tab.21, B.366 | R, S | 494(M + 1)+ |
| Tab.21, B.367 | R, S | 504(M + 1)+ |
| Tab.21, B.368 | R, S | 504(M + 1)+ |
| Tab.21, B.369 | R, S | 509(M + 1)+ |
| Tab.21, B.370 | R, S | 510(M + 1)+ |
| Tab.21, B.371 | R, S | 518(M + 1)+ |
| Tab.21, B.372 | R, S | 519(M + 1)+ |
| Tab.21, B.373 | R, S | 534(M + 1)+ |
| Tab.21, B.374 | R, S | 534(M + 1)+ |
| Tab.21, B.376 | R, S | 543(M + 1)+ |
| Tab.21, B.377 | R, S | 553(M + 1)+ |
| Tab.21, B.378 | R, S | 558(M + 1)+ |
| Tab.21, B.379 | R, S | 559(M + 1)+ |
| Tab.21, B.381 | R, S | 562(M + 1)+ |
| Tab.24, B.3 | R, S | 119–127° C. |
| Tab.25, B.3 | R, S | 143–149° C. |
| Tab.27, B.3 | diastereomere A (rac.) | 587(M − 1)− |
| Tab.27, B.3 | diastereomere B (rac.) | 587(M − 1)− |
| Tab.30, B.3 | R, S | oil |
| Tab.30, B.334 | R, S | 135–137° C. |
| Tab.32, B.3 | R, S | 142–144° C. |
| Tab.32, B.334 | R, S | 156–157° C. |
| Tab.36, B.3 | R, S | 171–178° C. |
| Tab.40, B.3 | R, S | 151–158° C. |
| Tab.47, B.3 | R, S | 145–147° C. |
| Tab.48, B.3 | R, S | 156–158° C. |
| Tab.49, B.3 | R, S | 144–148° C. |
| Tab.50, B.3 | R, S | 123–126° C. |

(M(ESMS) = ion peaks in electrospray massspectrometry)

TABLE D

Ugi intermediates

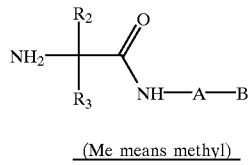
(VI)

(Me means methyl)

| No. | $R_2$ | $R_3$ | A | B | phys. data m.p. °C. |
|---|---|---|---|---|---|
| D1 | H | 4-Cl,3-F-phenyl | —CH$_2$CH$_2$— | 3,4-di-MeO-phenyl | oil |
| D2 | H | 4-Cl,3-CF$_3$-phenyl | —CH$_2$CH$_2$— | 3,4-di-MeO-phenyl | oil |
| D3 | H | 4-Cl,3-F-phenyl | —CH$_2$CH$_2$— | 4-n-butylO,3-MeO-phenyl | 94–97 |
| D4 | H | 3,4-di-Cl-phenyl | —CH$_2$CH$_2$— | 3,4-di-MeO-phenyl | oil |
| D5 | H | 4-Br-phenyl | —CH$_2$CH$_2$— | 3,4-di-MeO-phenyl | oil |
| D6 | H | 4-Me-phenyl | —CH$_2$CH$_2$— | 3,4-di-MeO-phenyl | 95–97 |
| D7 | H | 4-CF$_3$O-phenyl | —CH$_2$CH$_2$— | 3,4-di-MeO-phenyl | oil |
| D8 | H | 3,4-di-MeO-phenyl | —CH$_2$CH$_2$— | 3,4-di-MeO-phenyl | oil |
| D9 | H | 4-N(Me)$_2$-phenyl | —CH$_2$CH$_2$— | 3,4-di-MeO-phenyl | oil |
| D10 | H | 4-MeS-phenyl | —CH$_2$CH$_2$— | 3,4-di-MeO-phenyl | 71–75 |
| D11 | H | 3-Me-phenyl | —CH$_2$CH$_2$— | 3,4-di-MeO-phenyl | oil |
| D12 | H | 3-CF$_3$-phenyl | —CH$_2$CH$_2$— | 3,4-di-MeO-phenyl | oil |
| D13 | H | 4-PhO-phenyl | —CH$_2$CH$_2$— | 3,4-di-MeO-phenyl | oil |
| D14 | H | 4-EtO-phenyl | —CH$_2$CH$_2$— | 3,4-di-MeO-phenyl | 100–102 |
| D15 | H | 3,4-(OCH$_2$O)-phenyl | —CH$_2$CH$_2$— | 3,4-di-MeO-phenyl | oil |
| D16 | H | 4-Ph-phenyl | —CH$_2$CH$_2$— | 3,4-di-MeO-phenyl | oil |
| D17 | H | 4-i-propyl-phenyl | —CH$_2$CH$_2$— | 3,4-di-MeO-phenyl | 87–91 |
| D18 | H | 4-(COOMe)-phenyl | —CH$_2$CH$_2$— | 3,4-di-MeO-phenyl | 99–101 |
| D19 | H | 3,4-di-F-phenyl | —CH$_2$CH$_2$— | 3,4-di-MeO-phenyl | oil |
| D20 | H | 4-tert.butyl-phenyl | —CH$_2$CH$_2$— | 3,4-di-MeO-phenyl | 83–87 |
| D21 | H | 4-CN-phenyl | —CH$_2$CH$_2$— | 3,4-di-MeO-phenyl | oil |
| D22 | H | 3-Cl-phenyl | —CH$_2$CH$_2$— | 3,4-di-MeO-phenyl | oil |
| D23 | H | 1-naphthyl | —CH$_2$CH$_2$— | 3,4-di-MeO-phenyl | oil |
| D24 | H | 3,5-di-Cl-phenyl | —CH$_2$CH$_2$— | 3,4-di-MeO-phenyl | oil |
| D25 | H | 2-thienyl | —CH$_2$CH$_2$— | 3,4-di-MeO-phenyl | oil |
| D26 | H | 4-Cl-phenyl | —CH$_2$CH$_2$— | 3-MeO,4-propargylO-phenyl | oil |
| D27 | H | 2-furanyl | —CH$_2$CH$_2$— | 3,4-di-MeO-phenyl | oil |
| D28 | H | 4-Ph-phenyl | —CH$_2$CH$_2$— | 3-MeO,4-propargylO-phenyl | oil |
| D29 | H | 4-Cl-phenyl | —CH(CH$_3$)CH$_2$— | | oil |
| D30 | H | 4-Br-phenyl | —CH$_2$CH$_2$— | 3-MeO,4-propargylO-phenyl | oil |
| D31 | H | 4-Me-phenyl | —CH$_2$CH$_2$— | 3-MeO,4-propargylO-phenyl | oil |
| D32 | H | 4-Br-phenyl | —CH$_2$CH$_2$— | 3-MeO,4-(pent-2'-in-1'-yloxy)-phenyl | oil |
| D33 | H | 4-Me-phenyl | —CH$_2$CH$_2$— | 3-MeO,4-(pent-2'-in-1'-yloxy)-phenyl | oil |
| D34 | H | 2-naphthyl | —CH$_2$CH$_2$— | 3,4-di-MeO-phenyl | oil |
| D35 | H | 3,4-di-Cl-phenyl | —CH$_2$CH$_2$— | 3-MeO,4-propargylO-phenyl | oil |
| D36 | H | 4-Me-phenyl | —CH(CH$_3$)CH$_2$— | 3-MeO,4-propargylO-phenyl | oil |
| D37 | H | 5-Me,2-furanyl | —CH$_2$CH$_2$— | 3-MeO,4-allyO-phenyl | oil |
| D38 | H | 3-F-phenyl | —CH$_2$CH$_2$— | 3-MeO,4-allyO-phenyl | oil |
| D39 | H | 5-Me,2-thienyl | —CH$_2$CH$_2$— | 3-MeO,4-allyO-phenyl | oil |
| D40 | H | 4-MeO-phenyl | —CH$_2$CH$_2$— | 3-MeO,4-allyO-phenyl | oil |
| D41 | H | 2-MeO-phenyl | —CH$_2$CH$_2$— | 3-MeO,4-allyO-phenyl | oil |
| D42 | H | 3-Cl-phenyl | —CH$_2$CH$_2$— | 3-MeO,4-allyO-phenyl | oil |
| D43 | H | 2-Cl-phenyl | —CH$_2$CH$_2$— | 3-MeO,4-allyO-phenyl | oil |
| D44 | H | 3,5-di-F-phenyl | —CH$_2$CH$_2$— | 3-MeO,4-allyO-phenyl | oil |
| D45 | H | 3-Me,4-MeO-phenyl | —CH$_2$CH$_2$— | 3-MeO,4-allyO-phenyl | oil |
| D46 | H | 4-N-acetylamino-phenyl | —CH$_2$CH$_2$— | 3-MeO,4-allyO-phenyl | oil |
| D47 | H | 4-(COOMe)-phenyl | —CH$_2$CH$_2$— | 3-MeO,4-allyO-phenyl | oil |
| D48 | H | 3,5-di-MeO-phenyl | —CH$_2$CH$_2$— | 3-MeO,4-allyO-phenyl | oil |
| D49 | H | 2,4-di-MeO-phenyl | —CH$_2$CH$_2$— | 3-MeO,4-allyO-phenyl | oil |
| D50 | H | 2,4-di-Cl-phenyl | —CH$_2$CH$_2$— | 3-MeO,4-allyO-phenyl | oil |
| D51 | H | 3-(N-pyrrolidino)-phenyl | —CH$_2$CH$_2$— | 3-MeO,4-allyO-phenyl | oil |
| D52 | H | 4-Ph-phenyl | —CH$_2$CH$_2$— | 3-MeO,4-allyO-phenyl | oil |
| D53 | H | 3-Br-phenyl | —CH$_2$CH$_2$— | 3-MeO,4-allyO-phenyl | oil |
| D54 | H | 3-MeO,4-propargylO-phenyl | —CH$_2$CH$_2$— | 3-MeO,4-allyO-phenyl | oil |

TABLE D-continued

Ugi intermediates $$\text{NH}_2-\overset{R_2}{\underset{R_3}{C}}-\overset{O}{\underset{}{C}}-\text{NH}-A-B \qquad (VI)$$

(Me means methyl)

| No. | R₂ | R₃ | A | B | phys. data m.p. ° C. |
|---|---|---|---|---|---|
| D55 | H | 3-Br,2-thienyl | —CH₂CH₂— | 3-MeO,4-allyO-phenyl | oil |
| D56 | H | 3-fluorenyl | —CH₂CH₂— | 3-MeO,4-allyO-phenyl | oil |
| D57 | H | 3-(4'-Cl—PhO)-phenyl | —CH₂CH₂— | 3-MeO,4-allyO-phenyl | oil |
| D58 | H | 5-Me,2-furanyl | —CH₂CH₂— | 3-MeO,4-propargylO-phenyl | oil |
| D59 | H | 3-F-phenyl | —CH₂CH₂— | 3-MeO,4-propargylO-phenyl | oil |
| D60 | H | 5-Me,2-thienyl | —CH₂CH₂— | 3-MeO,4-propargylO-phenyl | oil |
| D61 | H | 4-MeO-phenyl | —CH₂CH₂— | 3-MeO,4-propargylO-phenyl | oil |
| D62 | H | 2-MeO-phenyl | —CH₂CH₂— | 3-MeO,4-propargylO-phenyl | oil |
| D63 | H | 3-MeO-phenyl | —CH₂CH₂— | 3-MeO,4-propargylO-phenyl | oil |
| D64 | H | 3-Cl-phenyl | —CH₂CH₂— | 3-MeO,4-propargylO-phenyl | oil |
| D65 | H | 2-Cl-phenyl | —CH₂CH₂— | 3-MeO,4-propargylO-phenyl | oil |
| D66 | H | 3,5-di-F-phenyl | —CH₂CH₂— | 3-MeO,4-propargylO-phenyl | oil |
| D67 | H | 3-Me,4-MeO-phenyl | —CH₂CH₂— | 3-MeO,4-propargylO-phenyl | oil |
| D68 | H | 4-NO₂-phenyl | —CH₂CH₂— | 3-MeO,4-propargylO-phenyl | oil |
| D69 | H | 4-N-acetylamino-phenyl | —CH₂CH₂— | 3-MeO,4-propargylO-phenyl | oil |
| D70 | H | 4-(COOMe)-phenyl | —CH₂CH₂— | 3-MeO,4-propargylO-phenyl | oil |
| D71 | H | 3,5-di-MeO-phenyl | —CH₂CH₂— | 3-MeO,4-propargylO-phenyl | oil |
| D72 | H | 2,4-di-Cl-phenyl | —CH₂CH₂— | 3-MeO,4-propargylO-phenyl | oil |
| D73 | H | 4-(N-pyrrolidino)-phenyl | —CH₂CH₂— | 3-MeO,4-propargylO-phenyl | oil |
| D74 | H | 3-Br-phenyl | —CH₂CH₂— | 3-MeO,4-propargylO-phenyl | oil |
| D75 | H | 3-MeO,4-propargylO-phenyl | —CH₂CH₂— | 3-MeO,4-propargylO-phenyl | oil |
| D76 | H | 4-Br,2-thienyl | —CH₂CH₂— | 3-MeO,4-propargylO-phenyl | oil |
| D77 | H | 3-fluorenyl | —CH₂CH₂— | 3-MeO,4-propargylO-phenyl | oil |
| D78 | H | 4-(4'-Cl—PhO)-phenyl | —CH₂CH₂— | 3-MeO,4-propargylO-phenyl | oil |
| D79 | H | 2,4-di-MeO-phenyl | —CH₂CH₂— | 3-MeO,4-propargylO-phenyl | oil |
| D80 | H | 5-Me,2-furanyl | —CH₂CH₂— | 3-MeO,4-(pent-2'-in-1'-yloxy)-phenyl | oil |
| D81 | H | 3-F-phenyl | —CH₂CH₂— | 3-MeO,4-(pent-2'-in-1'-yloxy)-phenyl | oil |
| D82 | H | 5-Me,2-thienyl | —CH₂CH₂— | 3-MeO,4-(pent-2'-in-1'-yloxy)-phenyl | oil |
| D83 | H | 4-MeO-phenyl | —CH₂CH₂— | 3-MeO,4-(pent-2'-in-1'-yloxy)-phenyl | oil |
| D84 | H | 2-MeO-phenyl | —CH₂CH₂— | 3-MeO,4-(pent-2'-in-1'-yloxy)-phenyl | oil |
| D85 | H | 3-MeO-phenyl | —CH₂CH₂— | 3-MeO,4-(pent-2'-in-1'-yloxy)-phenyl | oil |
| D86 | H | 2-Cl-phenyl | —CH₂CH₂— | 3-MeO,4-(pent-2'-in-1'-yloxy)-phenyl | oil |
| D87 | H | 3,5-di-F-phenyl | —CH₂CH₂— | 3-MeO,4-(pent-2'-in-1'-yloxy)-phenyl | oil |
| D88 | H | 3-Me,4-MeO-phenyl | —CH₂CH₂— | 3-MeO,4-(pent-2'-in-1'- | oil |

TABLE D-continued

Ugi intermediates $$\text{NH}_2-\underset{R_3}{\overset{R_2}{\text{C}}}-\underset{\text{NH}-A-B}{\overset{O}{\text{C}}}$$

(VI)

(Me means methyl)

| No. | R$_2$ | R$_3$ | A | B | phys. data m.p. °C. |
|---|---|---|---|---|---|
| D89 | H | 4-NO$_2$-phenyl | —CH$_2$CH$_2$— | 3-MeO,4-(pent-2'-in-1'-yloxy)-phenyl | oil |
| D90 | H | 4-(COOMe)-phenyl | —CH$_2$CH$_2$— | 3-MeO,4-(pent-2'-in-1'-yloxy)-phenyl | oil |
| D91 | H | 3,5-di-MeO-phenyl | —CH$_2$CH$_2$— | 3-MeO,4-(pent-2'-in-1'-yloxy)-phenyl | oil |
| D92 | HG | 2,4-di-MeO-phenyl | —CH$_2$CH$_2$— | 3-MeO,4-(pent-2'-in-1'-yloxy)-phenyl | oil |
| D93 | H | 2,4-di-Cl-phenyl | —CH$_2$CH$_2$— | 3-MeO,4-(pent-2'-in-1'-yloxy)-phenyl | oil |
| D94 | H | 4-(N-pyrrolidino)-phenyl | —CH$_2$CH$_2$— | 3-MeO,4-(pent-2'-in-1'-yloxy)-phenyl | oil |
| D95 | H | 3-Br-phenyl | —CH$_2$CH$_2$— | 3-MeO,4-(pent-2'-in-1'-yloxy)-phenyl | oil |
| D96 | H | 3-MeO,4-propargylO-phenyl | —CH$_2$CH$_2$— | 3-MeO,4-(pent-2'-in-1'-yloxy)-phenyl | oil |
| D97 | H | 4-Br,2-thienyl | —CH$_2$CH$_2$— | 3-MeO,4-(pent-2'-in-1'-yloxy)-phenyl | oil |
| D98 | H | 3-fluorenyl | —CH$_2$CH$_2$— | 3-MeO,4-(pent-2'-in-1'-yloxy)-phenyl | oil |
| D99 | H | 4-(4'-Cl—PhO)-phenyl | —CH$_2$CH$_2$— | 3-MeO,4-(pent-2'-in-1'-yloxy)-phenyl | oil |
| D100 | H | 5-Me,2-furanyl | —CH$_2$CH$_2$— | 3,4-di-MeO-phenyl | oil |
| D101 | H | 3-F-phenyl | —CH$_2$CH$_2$— | 3,4-di-MeO-phenyl | oil |
| D102 | H | 5-Me,2-thienyl | —CH$_2$CH$_2$— | 3,4-di-MeO-phenyl | oil |
| D103 | H | 4-MeO-phenyl | —CH$_2$CH$_2$— | 3,4-di-MeO-phenyl | oil |
| D104 | H | 2-MeO-phenyl | —CH$_2$CH$_2$— | 3,4-di-MeO-phenyl | oil |
| D105 | H | 3-MeO-phenyl | —CH$_2$CH$_2$— | 3,4-di-MeO-phenyl | oil |
| D106 | H | 2-Cl-phenyl | —CH$_2$CH$_2$— | 3,4-di-MeO-phenyl | oil |
| D107 | H | 3,5-di-F-phenyl | —CH$_2$CH$_2$— | 3,4-di-MeO-phenyl | oil |
| D108 | H | 3-Me,4-MeO-phenyl | —CH$_2$CH$_2$— | 3,4-di-MeO-phenyl | oil |
| D109 | H | 4-NO$_2$-phenyl | —CH$_2$CH$_2$— | 3,4-di-MeO-phenyl | oil |
| D110 | H | 4-(N-acetylamino)-phenyl | —CH$_2$CH$_2$— | 3,4-di-MeO-phenyl | oil |
| D111 | H | 3,5-di-MeO-phenyl | —CH$_2$CH$_2$— | 3,4-di-MeO-phenyl | oil |
| D112 | H | 2,4-di-MeO-phenyl | —CH$_2$CH$_2$— | 3,4-di-MeO-phenyl | oil |
| D113 | H | 2,4-di-Cl-phenyl | —CH$_2$CH$_2$— | 3,4-di-MeO-phenyl | oil |
| D114 | H | 4-(N-pyrrolidino)-phenyl | —CH$_2$CH$_2$— | 3,4-di-MeO-phenyl | oil |
| D115 | H | 3-Br-phenyl | —CH$_2$CH$_2$— | 3,4-di-MeO-phenyl | oil |
| D116 | H | 3-MeO,4-propargylO-phenyl | —CH$_2$CH$_2$— | 3,4-di-MeO-phenyl | oil |
| D117 | H | 4-Br,2-thienyl | —CH$_2$CH$_2$— | 3,4-di-MeO-phenyl | oil |
| D118 | H | 3-fluorenyl | —CH$_2$CH$_2$— | 3,4-di-MeO-phenyl | oil |
| D119 | H | 4-(4'-Cl—PhO)-phenyl | —CH$_2$CH$_2$— | 3,4-di-MeO-phenyl | oil |

Formulation Examples for Compounds of Formula I

Working procedures for preparing formulations of the compounds of formula I such as Emulsifiable concentrates, Solutions, Granulates, Dusts and Wettable powders are described in WO 97/33890.

Biological Examples

B-1: Action Against Plasmopara Viticola on Vines a) Residual-protective Action

Vine seedlings are sprayed at the 4- to 5-leaf stage with a spray mixture (0.02% active ingredient) prepared from a wettable powder formulation of the test compound. After 24 hours, the treated plants are infected with a sporangia suspension of the fungus. Fungus infestation is evaluated after incubation for 6 days at 95–100% relative humidity and 20° C.

b) Residual-curative Action

Vine seedlings are infected at the 4- to 5-leaf stage with a sporangia suspension of the fungus. After incubation for 24 hours in a humidity chamber at 95–100% relative humidity and 20° C., the infected plants are dried and sprayed with a spray mixture (0.02% active ingredient) prepared from a wettable powder formulation of the test compound. After the spray coating has dried, the treated plants are placed in the humidity chamber again. Fungus infestation is evaluated 6 days after infection.

Compounds of Tables 1 to 50 exhibit a very good fungicidal action against *Plasmopara viticola* on vines. Compounds Tab.14,B.203; Tab.14,B.319; Tab.14,B.335; Tab.14, B.336; Tab.15,B.3; Tab.17,B.1; Tab.17,B.3; Tab.17,B.82; Tab.17,B.88; Tab.17,B.251; Tab.21,B.3; Tab.21,B.88; Tab.21,B.319; Tab.24,B.3 and others virtually completely inhibit fungal infestation (0 to 10% infestation) in this test. On the other hand, Plasmopara infestation on untreated and infected control plants is 100%.

B-2: Action Against Phytophthora on Tomato Plants a) Residual-protective Action

After a cultivation period of 3 weeks, tomato plants are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90–100% relative humidity and 20° C.

b) Systemic Action

After a cultivation period of 3 weeks, tomato plants are watered with a spray mixture (0.02% active ingredient based on the volume of the soil) prepared from a wettable powder formulation of the test compound. Care is taken that the spray mixture does not come into contact with the parts of the plants which are above ground. After 4 days, the treated plants are infected with a sporangia suspension of the fungus. Fungus infestation is evaluated after incubation of the infected plants for 4days at 90–100% relative humidity and 20° C. Compounds of Tables 1 to 50 exhibit a lasting effect (less than 20% fungus infestation). Infestation is prevented virtually completely (0 to 5% infestation) with compounds Tab.14,B.1 12; Tab.14,B.203; Tab.14,B.335; Tab.14,B.336; Tab.15,B.3; Tab.17B.1; Tab.17,B.3; Tab.17, B.82; Tab.17,B.85; Tab.17,B.88; Tab.17,B.251; Tab.18,B.3; Tab.21,B.3; Tab.21,B.88; Tab.21,B.319 and others. On the other hand, Phytophthora infestation on untreated and infected control plants is 100%.

B-3 Action Against Phytophthora on Potato Plants a) Residual-protective Action

2–3 week old potato plants (Bintje variety) are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90–100% relative humidity and 20° C.

b) Systemic Action

2–3 week old potato plants (Bintje variety) are watered with a spray mixture (0.02% active ingredient based on the volume of the soil) prepared from a wettable powder formulation of the test compound. Care is taken that the spray mixture does not come into contact with the parts of the plants which are above ground. After 48 hours, the treated plants are infected with a sporangia suspension of the fungus. Fungus infestation is evaluated after incubation of the infected plants for 4 days at 90–100% relative humidity and 20° C. Compounds of Tables 1 to 50 exhibit a lasting effect (less than 20% fungus infestation). Infestation is prevented virtually completely (0 to 5% infestation) with compounds Tab.14,B.38; Tab.14,B.203; Tab.14,B.319; Tab.15,B.3; Tab.17,B.1; Tab.17,B.3; Tab.17,B.82; Tab.17, B.85; Tab.17,B.88; Tab.17,B.251 and others. On the other hand, Phytophthora infestation on untreated and infected control plants is 100%.

What is claimed is:

1. A compound of formula I

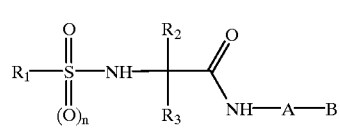

wherein n is the number zero or one;

$R_1$ is optionally substituted alkyl, alkenyl, alkynyl, cycloalkyl, cycloalkylalkyl, aryl or arylalkyl; or a group $NR_aR_b$ wherein $R_a$ and $R_b$ are each independently of the other hydrogen, alkyl or form together an alkylene bridge;

$R_2$ is hydrogen or alkyl;

$R_3$ is optionally substituted aryl or heteroaryl;

A is alkylene; and

B is optionally substituted aryl;

with the exception of the following compounds 2-phenyl-N-(1-phenyl-ethyl)-2-(4-aminophenyl)-sulfonylamino-acetamide, 2-phenyl-N-(1-phenyl-ethyl)-2-(4-methylphenyl)-sulfonylamino-acetamide, 2-phenyl-N-(1-phenyl-ethyl)-2-(4-chlorophenyl)-sulfonylamino-acetamide, 2-phenyl-N-(1-phenyl-ethyl)-2-(4-nitrophenyl)-sulfonylamino-acetamide, 2-phenyl-N-(1-phenyl-ethyl)-2-(4-methoxyphenyl)-sulfonylamino-acetamide, 2-phenyl-N-(1-phenyl-ethyl)-2-(4-fluorophenyl)-sulfonylamino-acetamide, 2-phenyl-N-(1-phenyl-ethyl)-2-phenyl-sulfonylamino-acetamide and 2-phenyl-N-(1-phenyl-ethyl)-2-methane-sulfonylamino-acetamide.

2. A compound of formula I according to claim 1, wherein n is the number zero or one;

$R_1$ is $C_1$–$C_{10}$alkyl, $C_2$–$C_{10}$alkenyl, $C_2$–$C_{10}$alkynyl, $C_3$–$C_8$cycloalkyl, $C_3$–$C_8$cycloalkyl-$C_1$–$C_6$alkyl, $C_1$–$C_{10}$aryl, or $C_6$–$C_{10}$aryl-$C_1$–$C_6$alkyl that are optionally mono- or poly-substituted by $C_1$–$C_8$alkyl, $C_1$–$C_8$alkoxy, $C_1$–$C_8$alkylthio, $C_1$–$C_8$alkylsulfonyl, $C_3$–$C_8$cycloalkyl, $C_1$–$C_8$alkoxycarbonyl, $C_3$–$C_8$alkenyloxycarbonyl, $C_3$–$C_8$alkynyloxycarbonyl, $C_3$–$C_8$cycloalkyl-$C_1$–$C_6$alkyl, $C_2$–$C_8$alkenyl, $C_2$–$C_8$alkynyl, $C_3$–$C_8$alkenyloxy, $C_3$–$C_8$alkynyloxy, $C_1$–$C_8$alkanoyl (where all these alkyl, alkenyl, alkynyl or cycloalkyl containing groups may be partially or fully halogenated), halogen, cyano or nitro; or a group $NR_aR_b$, wherein $R_a$ and $R_b$ are each independently of the other hydrogen, $C_1$–$C_8$alkyl or together are $C_2$–$C_7$alkylen;

$R_2$ is hydrogen or $C_1$–$C_8$alkyl;

$R_3$ is phenyl, naphthyl or heteroaryl formed by 1 or 2 five- or six-membered rings containing 1 to 4 identical or different heteroatoms selected from oxygen, nitrogen or sulfur and are optionally mono- or poly-substituted by $C_1$–$C_8$alkyl, $C_2$–$C_8$alkenyl, $C_2$–$C_8$alkynyl, $C_1$–$C_8$alkoxy, $C_1$–$C_8$alkylthio, $C_1$–$C_8$alkylsulfonyl, $C_3$–$C_8$cycloalkyl, $C_3$–$C_8$cycloalkyl-$C_1$–$C_6$alkyl, $C_1$–$C_8$alkoxycarbonyl, $C_3$–$C_8$alkenyloxycarbonyl, $C_3$–$C_8$alkynyloxycarbonyl, $C_1$–$C_4$alkylendioxy, $C_3$–$C_8$cycloalkyloxy, $C_3$–$C_8$alkenyloxy, $C_3$–$C_8$alkynyloxy, $C_1$–$C_8$alkanoyl, $C_1$–$C_8$dialkylamino, $C_1$–$C_8$alkylamino (where all these alkyl alkenyl, alkynyl or cycloalkyl containing groups may be partially or fully halogenated), halogen, nitro, cyano, hydroxy or amino;

A is $C_1$–$C_8$alkylen; and

B is phenyl optionally mono- or poly-substituted by $C_1$–$C_8$alkyl, $C_2$–$C_8$alkenyl, $C_2$–$C_8$alkynyl, $C_1$–$C_8$alkoxy, $C_1$–$C_8$alkylthio, $C_1$–$C_8$alkylsulfonyl, $C_3$–$C_8$cycloalkyl, $C_3$–$C_8$cycloalkyl-$C_1$–$C_6$alkyl, $C_1$–$C_8$alkoxycarbonyl, $C_3$–$C_8$alkenyloxycarbonyl, $C_3$–$C_8$alkynyloxycarbonyl, $C_3$–$C_8$cycloalkyloxy, $C_3$–$C_8$alkenyloxy, $C_3$–$C_8$alkynyloxy, $C_1$–$C_8$alkanoyl, $C_1$–$C_8$dialkylamino, $C_1$–$C_8$alkylamino, $C_6$–$C_{10}$aryloxy, $C_6$–$C_{10}$aryl-$C_1$–$C_6$alkoxy, $C_6$–$C_{10}$aryl-$C_1$–$C_6$alkenyloxy, $C_6$–$C_{10}$aryl-$C_1$–$C_6$alkynyloxy, $C_1$–$C_8$alkanoyloxy (where all these alkyl alkenyl, alkynyl or cycloalkyl containing groups may be partially or fully halogenated and where all aryl containing groups may be optionally mono- or poly-substituted by $C_1$–$C_8$alkyl, $C_2$–$C_8$alkenyl $C_3$–$C_8$cycloalkyl, $C_1$–$C_8$alkoxy, $C_1$–$C_8$alkylthio, $C_1$–$C_8$alkoxycarbonyl $C_1$–$C_8$halogenalkyl, $C_1$–$C_8$halogenalkoxy, $C_1$–$C_8$halogenthioalkyl, halogen nitro or cyano), halogen, nitro, cyano, hydroxy, amino or the phenyl group may be substituted in two adjacent positions by $C_1$–$C_4$alkylenedioxy wherein the alkylene part may be substituted by halogen.

3. A compound of formula I according to claim 2, wherein n is the number zero or one;

$R_1$ is $C_1$–$C_{10}$alkyl $C_2$–$C_{10}$alkenyl, $C_3$–$C_8$cycloalkyl that are optionally mono- or poly-substituted by $C_1$–$C_8$alkyl, $C_1$–$C_8$alkoxy, $C_1$–$C_8$alkylthio, $C_1$–$C_8$alkanoyl, $C_1$–$C_8$alkoxycarbonyl, $C_1$–$C_8$halogenalkyl, $C_1$–$C_8$halogenalkoxy, $C_1$–$C_8$halogenalkylthio, halogen, nitro or cyano; or a group $NR_aR_b$, wherein $R_a$ and $R_b$ are each independently of the other hydrogen, $C_1$–$C_8$alkyl, or together are tetramethylene or pentamethylene;

$R_2$ is hydrogen or methyl;

$R_3$ is phenyl, naphthyl, furyl, thienyl, imidazolyl, thiazolyl, oxazolyl, pyridyl, pyrimidinyl, benzothiophenyl, benzothiazolyl, chinolinyl, pyrazolyl, indolyl, benzimidazolyl or pyrrolyl optionally substituted by 1 to 3 substituents selected from $C_1$–$C_8$alkyl, $C_2$–$C_8$alkenyl, $C_3$–$C_8$cycloalkyl, $C_1$–$C_8$alkoxy, $C_1$–$C_8$alkylthio, $C_1$–$C_8$alkoxycarbonyl, $C_1$–$C_8$halogenalkyl, $C_1$–$C_8$halogenalkoxy, $C_1$–$C_8$halogenalkylthio, halogen, hydroxy, nitro or cyano;

A is $C_1$–$C_4$alkylen; and

B is phenyl optionally substituted by 1 to 3 substituents selected from $C_1$–$C_8$alkyl, $C_1$–$C_8$alkoxy, $C_3$–$C_8$alkenyloxy, $C_3$–$C_8$alkynyloxy, phenyl-$C_1$–$C_6$alkyloxy, phenyl-$C_3$–$C_6$alkenyloxy, phenyl-$C_3$–$C_6$alkynyloxy, $C_1$–$C_8$alkylthio, $C_1$–$C_8$alkoxycarbonyl, $C_1$–$C_8$halogenalkoxy, $C_3$–$C_8$halogenalkenyloxy, halogen, hydroxy, nitro or cyano (where all phenyl containing groups may be optionally substituted by 1 to 3 substituents selected from $C_1$–$C_8$alkyl, $C_1$–$C_8$alkoxy, $C_1$–$C_8$alkylthio, $C_1$–$C_8$halogenalkyl, $C_1$–$C_8$halogenalkoxy, $C_1$–$C_8$halogenthioalkyl, halogen or cyano).

4. A compound of formula I according to claim 3, wherein n is the number one;

$R_1$ is $C_1$–$C_6$alkyl, $C_2$–$C_{10}$alkenyl, $C_5$–$C_6$cycloalkyl, that are optionally mono- or poly-substituted by $C_1$–$C_8$alkyl, $C_1$–$C_8$alkoxy, $C_1$–$C_8$alkoxycarbonyl, $C_1$–$C_8$halogenalkyl, $C_1$–$C_8$halogenalkoxy, halogen or cyano; or a group $NR_aR_b$, wherein $R_a$ and $R_b$ are each independently of the other methyl or ethyl;

$R_2$ is hydrogen;

$R_3$ is phenyl optionally substituted by 1 to 3 substituents selected from $C_1$–$C_8$alkyl, $C_2$–$C_8$alkenyl, $C_3$–$C_8$cycloalkyl, $C_1$–$C_8$alkoxy, $C_1$–$C_8$alkylthio, $C_1$–$C_8$alkoxycarbonyl, $C_1$–$C_8$halogenalkyl, $C_1$–$C_8$halogenalkoxy, $C_1$–$C_8$halogenthioalkyl, halogen, hydroxy, nitro or cyano;

A is ethylen; and

B is phenyl optionally substituted by 2 to 3 substituents selected from $C_1$–$C_8$alkyl, $C_1$–$C_8$alkoxy, $C_3$–$C_8$alkenyloxy, $C_3$–$C_8$alkynyloxy, phenyl-$C_1$–$C_6$alkyloxy, phenyl-$C_3$–$C_6$alkenyloxy, phenyl-$C_3$–$C_6$alkynyloxy, $C_1$–$C_8$alkylthio, $C_1$–$C_8$alkoxycarbonyl, $C_1$–$C_8$halogenalkoxy, $C_3$–$C_8$halogenalkenyloxy, halogen, hydroxy, nitro or cyano (where all phenyl containing groups may be optionally substituted by 1 to 3 substituents selected from $C_1$–$C_8$alkyl, $C_1$–$C_8$alkoxy, $C_1$–$C_8$alkylthio, $C_1$–$C_8$halogenalkyl, $C_1$–$C_8$halogenalkoxy, $C_1$–$C_8$halogenthioalkyl, halogen or cyano).

5. A compound of formula I according to claim 4, wherein n is the number one;

$R_1$ is $C_1$–$C_4$alkyl optionally mono- or poly-substituted by fluorine, chlorine, bromine or dimethylamin;

$R_2$ is hydrogen;

$R_3$ is phenyl optionally substituted by 1 to 3 substituents selected from $C_1$–$C_8$alkyl, $C_2$–$C_8$alkenyl, $C_3$–$C_8$cycloalkyl, $C_1$–$C_8$alkoxy, $C_1$–$C_8$alkylthio, $C_1$–$C_8$alkoxycarbonyl, $C_1$–$C_8$halogenalkyl, $C_1$–$C_8$halogenalkoxy, $C_1$–$C_8$halogenthioalkyl, halogen, nitro or cyano;

A is ethylen; and

B is a group

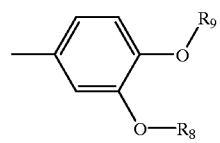

wherein $R_8$ is $C_1$–$C_4$alkyl, and $R_9$ is $C_1$–$C_8$alkyl, $C_3$–$C_8$alkenyl, $C_3$–$C_8$alkynyl, phenyl-$C_1$–$C_6$alkyl, phenyl-$C_3$–$C_6$alkenyl, phenyl-$C_3$–$C_6$alkynyl, $C_1$–$C_8$halogenalkyl, $C_3$–$C_8$halogenalkenyl (where all phenyl containing groups may be optionally substituted by 1 to 3 substituents selected from $C_1$–$C_8$alkyl, $C_1$–$C_8$alkoxy, $C_1$–$C_8$alkylthio, $C_1$–$C_8$halogenalkyl, $C_1$–$C_8$halogenalkoxy, $C_1$–$C_8$halogenthioalkyl, halogen or cyano).

6. A process for the preparation of a compound of formula I according to claim 1, which comprises a) reacting an amino acid of formula II or a carboxy-activated derivative of an amino acid of formula II

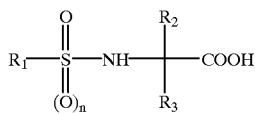 (II)

with an amine of the formula V

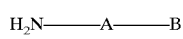 (V); or b) reacting a sulfonyl halide or sulfinyl halide of formula III

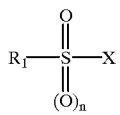 (III)

where X is halide, with an amino acid derivative of formula VI

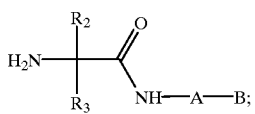 (VI)

and optionally c) oxidizing a compound of formula I wherein n=0 and wherein $R_1$, $R_2$, $R_3$, A and B have the meaning as defined for formula I to a compound of formula I wherein n=1.

7. A composition for controlling and preventing infestation of plants by microorganisms, which comprises as active ingredient a compound of formula I according to claim 1, together with a suitable carrier.

8. A method of controlling and preventing infestation of plants by microorganisms, which comprises applying a compound of formula I according to claim 1 as active ingredient to the plant, to parts of the plant or to the nutrient medium of the plant.

9. A method according to claim 8, which comprises treating seed.

10. The intermediate of formula VI

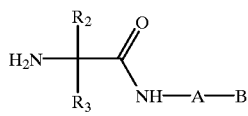 (VI)

wherein $R_2$, $R_3$, A and B are as defined in formula I.

11. A process for the preparation of a compound of formula VI according to claim 10, which comprises d) hydrolizing a compound of formula X

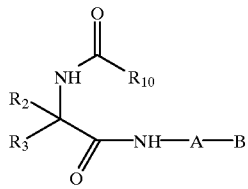 (X)

under acidic or basic conditions at a temperature between 0° and 100° C., wherein $R_2$, $R_3$, A and B have the meaning as defined for formula I and wherein $R_{10}$ is lower alkyl or hydrogen.

* * * * *